United States Patent
Nguyen et al.

(10) Patent No.: US 10,525,455 B2
(45) Date of Patent: Jan. 7, 2020

(54) CATALYST COMPOSITION AND PROCESS FOR PREPARING OLEFIN OXIDES

(71) Applicant: Northwestern University, Evanston, IL (US)

(72) Inventors: SonBinh T. Nguyen, Evanston, IL (US); Joseph T. Hupp, Northfield, IL (US); Omar K. Farha, Glenview, IL (US); Sergio J. Garibay, Chicago, IL (US)

(73) Assignee: NORTHWESTERN UNIVERSITY, Evanston, IL (US)

(*) Notice: Subject to any disclaimer, the term of this patent is extended or adjusted under 35 U.S.C. 154(b) by 0 days.

(21) Appl. No.: 15/953,659

(22) Filed: Apr. 16, 2018

(65) Prior Publication Data

US 2018/0297018 A1  Oct. 18, 2018

Related U.S. Application Data

(62) Division of application No. 14/800,358, filed on Jul. 15, 2015, now Pat. No. 9,943,839.

(60) Provisional application No. 62/024,515, filed on Jul. 15, 2014.

(51) Int. Cl.
| | | |
|---|---|---|
| *B01J 31/18* | (2006.01) | |
| *B01J 31/16* | (2006.01) | |
| *C07D 301/12* | (2006.01) | |
| *B01J 31/22* | (2006.01) | |
| *B01J 31/38* | (2006.01) | |

(52) U.S. Cl.
CPC ......... *B01J 31/182* (2013.01); *B01J 31/1691* (2013.01); *B01J 31/2239* (2013.01); *B01J 31/38* (2013.01); *C07D 301/12* (2013.01); *B01J 2231/72* (2013.01); *B01J 2531/0258* (2013.01)

(58) Field of Classification Search
CPC ........ C07D 301/12; B01J 31/182; B01J 31/38
See application file for complete search history.

(56) References Cited

U.S. PATENT DOCUMENTS

| | | |
|---|---|---|
| 3,635,841 A | 1/1972 | Cornely et al. |
| 5,329,024 A | 7/1994 | Jureller et al. |
| 8,497,387 B2 | 7/2013 | Marks et al. |

FOREIGN PATENT DOCUMENTS

| | | |
|---|---|---|
| CN | 101920213 A | 12/2010 |
| CN | 103151543 A | 6/2013 |
| CN | 103165912 A | 6/2013 |
| WO | 2000002872 A1 | 1/2000 |
| WO | 2010077483 A1 | 7/2010 |
| WO | 2011056381 A1 | 5/2011 |
| WO | 2011084687 A1 | 7/2011 |
| WO | 2013070392 A1 | 5/2013 |

OTHER PUBLICATIONS

IUPAC Project "Coordination Polymers and Metal Organic Frameworks" www.iupac.org/web/ins/2009-12-200, accessed Nov. 17, 2016.
Yin, F. et al., "Hydrothermal synthesis of alpha-MnO2/MIL-101(Cr) composite and its bifunctional electrocatalytic for oxygen reduction/evolution reactions", Catalysis Communications, 2014, 54, 17-21, published activity May 24, 2014.
U.S. Appl. No. 14/800,358, filed Jul. 15, 2015.

*Primary Examiner* — Noble E Jarrell
(74) *Attorney, Agent, or Firm* — Bell & Manning, LLC

(57) ABSTRACT

A catalyst composition comprising (a) a manganese-containing compound and (b) a carboxylic acid functionalized metal organic framework (MOF) compound; and a process for preparing an olefin oxide compound product including reacting (a) at least one olefin compound with (b) at least one oxidant in the presence of (c) the above catalyst composition.

15 Claims, 5 Drawing Sheets

*NU-1000-A$^L$ reversibly binds to Mn$_2$O$_3$(TMTACN)$_2$ with H$_2$O$_2$ resulting in the active Mn$^{III}$ epoxidation catalyst*

DVB epoxidation with NU-1000-A$^{L2-L4}$

The increased acidity of the carboxylic acids and subsequent faster catalyst binding facilitates faster DVB epoxidation and DVB-DO formation

CATALYST COMPOSITION AND PROCESS FOR PREPARING OLEFIN OXIDES

This application is a divisional of and claims priority to and the benefit of application Ser. No. 14/800,358 filed Jul. 15, 2015 and issued as U.S. Pat. No. 9,943,839 on Apr. 17, 2018, which claimed priority to and the benefit of application Ser. No. 62/024,515 filed Jul. 15, 2014—each of which is incorporated herein by reference in its entirety.

FIELD

The present invention is related to a catalyst composition and to a process using such catalyst composition for epoxidizing an olefin compound to prepare an olefin oxide compound. For example, the catalyst composition can be used for epoxidizing a divinylarene to prepare a divinylarene dioxide.

BACKGROUND

The epoxidation of olefins is a reaction process that typically uses a catalyst, and heretofore, various heterogeneous and homogeneous catalysts have been used in processes for the epoxidation of olefins. Known catalyst art includes the use of a manganese (Mn) complex catalyst for epoxidizing olefins. For example, U.S. Pat. No. 5,329,024 discloses using a homogeneous 1,4,7-trimethyl-1,4,7-triazacyclononane manganese complex, [Mn$_2$(TMTACN)$_2$ ($\mu$-O)$_3$](PF$_6$)$_2$.H$_2$O, as a catalyst, for epoxidizing olefins with hydrogen peroxide (H$_2$O$_2$) as an oxidizing agent. "TMTACN" herein stands for 1,4,7-trimethyl-1,4,7-triazacyclononane.

One disadvantage of the above manganese complex catalyst is that such catalyst does not work well in epoxidizing olefins because the above manganese complex catalyst exhibits catalase properties and the catalyst is known to readily decompose H$_2$O$_2$ into water (H$_2$O) and oxygen (O$_2$). Therefore, the decomposition of H$_2$O$_2$ by the known catalyst reduces epoxide product yield. The catalytic epoxidation system disclosed in U.S. Pat. No. 5,329,024, if used on an industrial process scale, would necessitate an excess and inefficient use of H$_2$O$_2$.

The undesirable catalase activity exhibited by the above [Mn$_2$(TMTACN)$_2$($\mu$-O)$_3$](PF$_6$)$_2$.H$_2$O complex (abbreviated herein as "(TMTACN)Mn") can be mitigated through the use of carboxylic acid additives. For instance, the use of the (TMTACN)Mn complex in conjunction with a carboxylic acid-grafted silica support can successfully epoxidize some specific olefins with more efficient utilization of H$_2$O$_2$. Turn over numbers (TON) of greater than (>) 600 are reached with the silica support, however, under identical acid-Mn ratios (e.g. >2:1), the homogeneous analogues of such catalysts produce less than (<) 65 TON (for example, as described in Schoenfeldt et al., *J. Am. Chem. Soc.*, 2011, 133, 18664-18695). Unfortunately, the use of these known carboxylic acid-tethered mesoporous silica (TMTACN)Mn complex catalysts produces ring-opening diols as undesired byproducts. For example, when (TMTACN)$_2$Mn$_2$O$_3$ is bound or tethered onto a solid support such as silica, cis-diols are produced as primary byproducts.

Ligand-tethered supports can also facilitate the epoxidation of olefins using (TMTACN)Mn complexes. For example, WO2000002872 discloses that a 65 percent (%) yield of styrene oxide is obtained through the use of a silica-tethered (DMTACN)Mn catalyst with a two-fold excess of H$_2$O$_2$. "DMTACN" herein stands for 1,4-dimethyl-1,4,7-triazacyclononane. For comparison, use of DMTACN in the absence of a ligand-tethered support produces only 5% yield of styrene oxide because of pronounced oxidant disintegration. WO2000002872 does not disclose the epoxidation of a divinylarene such as divinylbenzene (DVB). And, even though styrene and DVB are structurally similar, a catalyst capable of epoxidizing a mono-olefin such as styrene is not necessarily capable of epoxidizing a di-olefin such as DVB.

It is also known in the art that it is very difficult to obtain complete epoxidation of DVB to divinylbenzene dioxide (DVBDO) in an industrial process, because of the multiple terminal olefin groups present in DVB. Some of the multiple terminal olefin groups present in DVB are typically not fully converted to DVBDO using known epoxidation reaction processes; and therefore, an undesirable partially oxidized compound such as divinylbenzene monoxide (DVBMO) is generated. And, because DVBDO and DVBMO have similar boiling points, DVBDO cannot be easily separated from DVBMO except through very complex steps and costly separation operations.

Heretofore, a few catalytic epoxidation processes for the selective double epoxidation of DVB to DVBDO have been carried out with some degree of success. For example, WO2013070392A1 discloses a process for preparing a divinylarene dioxide by epoxidizing a divinylarene with H$_2$O$_2$ as the oxidizing agent and an iron-containing compound as the catalyst such that a yield of a divinylarene dioxide product of about 70% is obtained. However, the process disclosed in WO2013070392A1 uses a homogeneous catalyst and requires the addition of amine additives to achieve yields of about 70%.

U.S. Pat. No. 8,497,387 also discloses a catalytic epoxidation of a divinylarene with an oxidant in the presence of a catalyst and a solvent wherein the disclosed oxidant is a peroxycarboximidic acid. However, a peroxycarboximidic acid, used as an oxidant, generates stoichiometric amounts of amide organic byproduct waste, entailing multiple separation and purification steps to remove such waste. Thus, removal of the amide organic byproduct waste from the product produced using the process disclosed in U.S. Pat. No. 8,497,387 increases the complexity and cost of carrying out such process on an industrial scale.

It would advance the art of catalytic epoxidation of olefins to provide a catalyst or catalyst system useful for the epoxidation of an olefin reaction process that has low catalase activity; enhances epoxide selectivity, and increases reaction yield in the epoxidation of olefins. For example, the catalytic epoxidation of a divinylarene such as DVB to a divinylarene dioxide such as divinylbenzene dioxide (DVBDO) is a process that could be improved by using a catalyst that does not suffer from the aforementioned disadvantages of the currently known catalysts used in such a process.

In view of the above issues with the known prior art processes, it is desired to provide a novel catalyst composition and process for the catalytic epoxidation of olefins, such as a process for manufacturing DVBDO, that facilitates olefin dioxide formation in high yields (e.g., >70%) using low catalyst loadings (e.g. <5 mol %), while eliminating or at least mitigating: (i) the use of other additives and/or (ii) the generation of undesired byproduct waste.

SUMMARY

One aspect of the present invention is directed to a catalyst system (or catalyst composition) useful in a process for the selective catalytic epoxidation of an olefin compound to prepare an olefin oxide compound.

The catalyst composition includes (a) a manganese-containing compound and (b) a carboxylic acid functionalized metal organic framework (MOF) compound. For example, in one embodiment, the catalyst composition of the present invention includes a manganese triazacyclononane complex as component (a) and a chemically robust porous material tethered with carboxylic acid moieties as component (b). In another embodiment, the catalyst composition of the present invention may include, for example, a combination of a manganese triazacyclononane complex (e.g., 1,4,7-trimethyl-1,4,7-tri azacyclononane manganese complex such as [Mn$_2$(TMTACN)$_2$($\mu$-O)$_3$](PF$_6$)$_2$.H$_2$O)) plus a carboxylic acid-functionalized MOF compound (e.g., an acid ligand modified Zr$_6$(OH)$_8$(TBAPy)$_2$).

Another aspect of the present invention is directed to a process for the selective catalytic epoxidation of an olefin compound to prepare an olefin oxide compound in high yields (e.g., >70%).

The epoxidation process for preparing an olefin oxide compound product includes the step of reacting the following compounds: (a) an olefin compound; (b) an oxidant, and (c) a catalyst composition. The catalyst used in the catalytic epoxidation process includes the above-described catalyst composition. For example, in one embodiment, the process of the present invention may be carried out by epoxidizing an olefin such as a divinylarene (such as DVB) with H$_2$O$_2$ as the oxidant (or oxidizing agent) in the presence of the above-described catalyst composition which may include, for example, a combination of a manganese triazacyclononane complex and a carboxylic acid-functionalized MOF compound.

The reaction process to prepare the olefin oxide compound product can be advantageously carried out under mild conditions. "Mild conditions" herein can be for example at a temperature of <80° C. and atmospheric pressure in one embodiment; and at a temperature of <60° C. and atmospheric pressure in another embodiment. The performance of the present process under mild conditions avoids having to perform the process using complex and expensive process equipment. The epoxidation process of the present invention using the above catalyst composition also beneficially mitigates complex purification processes, ensures recovery of the catalyst composition, and makes production of an oxide product feasible on an industrial scale.

The process of the present invention has many other advantages including for example: (1) the heterogeneous acid-functionalized support used in the process is higher yielding and selective than its homogeneous analogues; (2) the process using the above catalyst composition produces high yields of an olefin oxide such as DVBDO (e.g., >90%); (3) the high yields of the olefin oxide such as DVBDO are produced within a short period of time (e.g., from 4-5 hours or less); (4) the high yields of the olefin oxide such as DVBDO are produced using a relatively low catalyst loading (e.g., <1 mol %); (5) the high yields of olefin oxide such as DVBDO are produced using an environmentally friendly oxidant such as H$_2$O$_2$; (6) the process produces very small amounts (e.g., <1%), of undesirable byproducts; (7) the process offers a facile separation and recovery of the carboxylic acid functionalized metal organic framework (MOF) compound through conventional separation operations such as filtration; (8) the carboxylic acid support platform used in the present invention is fully recoverable and regenerable and displays similar selective epoxidation upon reuse; and (9) the modular carboxylic acid functionalization approach used in the present invention allows for fine-tuning of catalytic oxidation properties.

BRIEF DESCRIPTION OF THE DRAWINGS

For the purpose of illustrating the present invention, the drawings show a form of the present invention which is presently preferred. However, it should be understood that the present invention is not limited to the embodiments shown in the drawings.

(FIG. 4A and FIG. 5) Schematic illustrations of DVB epoxidation; (FIGS. 4B-D) Graphic illustrations of alkene and product yields using NU-1000-A$^{L2-L4}$. (See, e.g., Examples 1, 2 and 4.)

DETAILED DESCRIPTION

Figure 1:
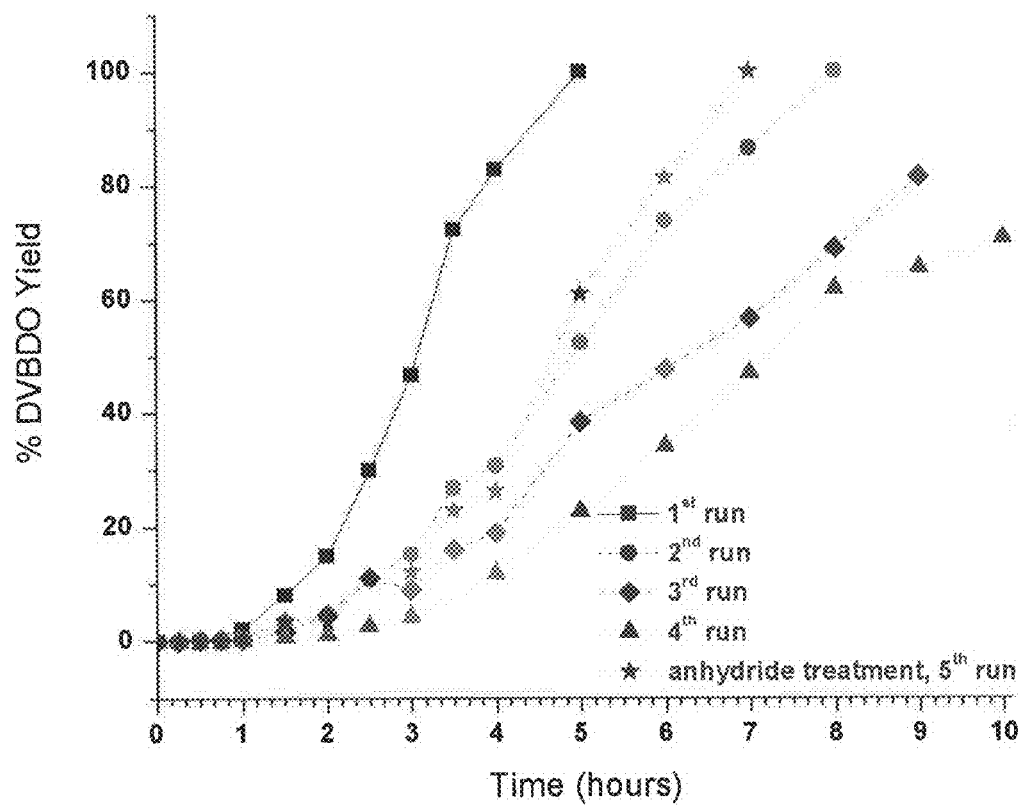
FIG. 1. Graphical illustration showing the effect of reactivating and reusing a catalyst of the present invention by plotting percent DVBDO yield versus time for 4 runs without reactivating the catalyst; and then after the 4 runs, reactivating the catalyst and running the process one more time.
Figure 2:
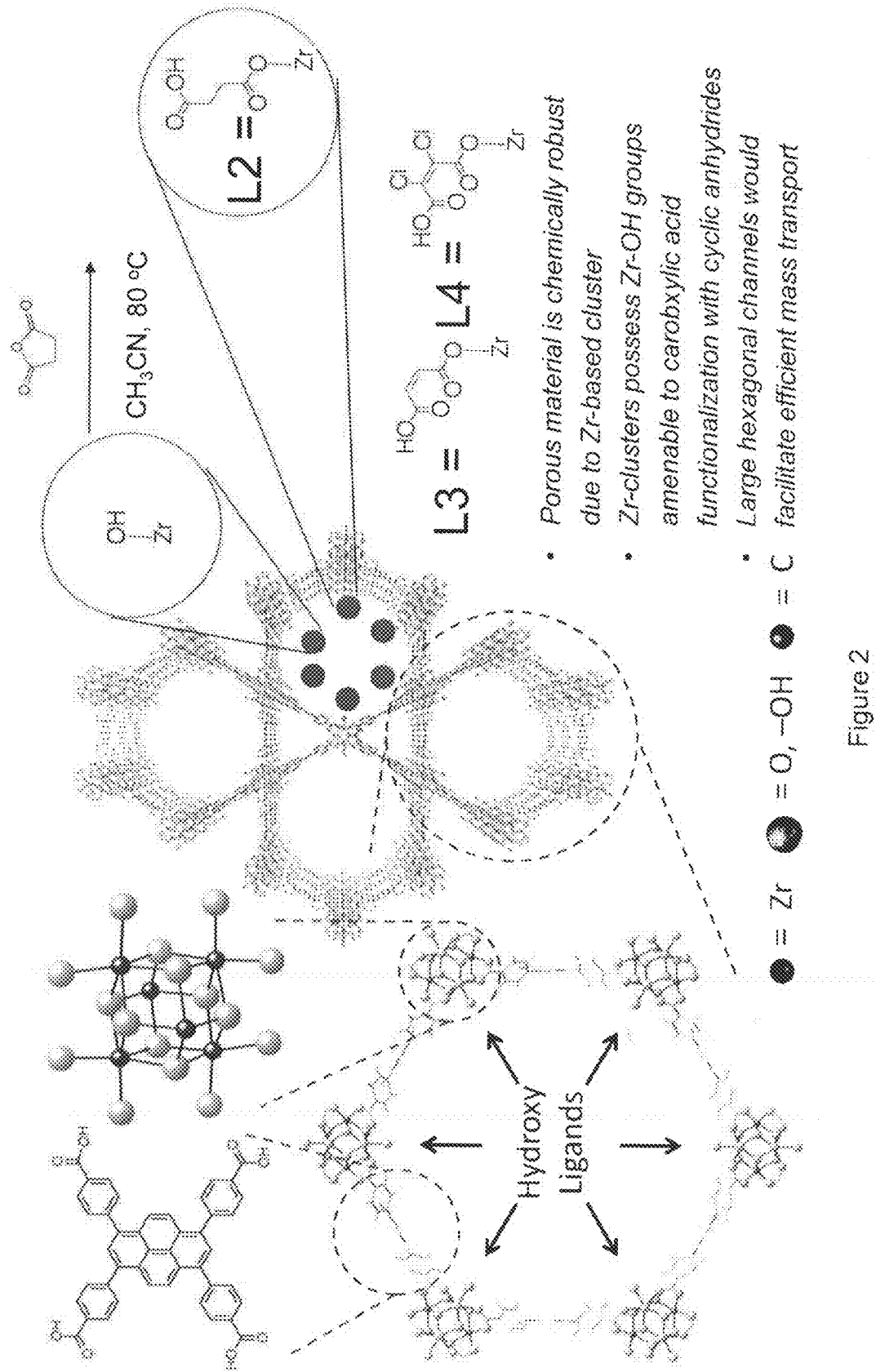
FIG. 2. Schematic illustration showing syntheses of NU-1000-A$^{L2-L4}$. (See, e.g., Examples II-IV.)
Figure 3:
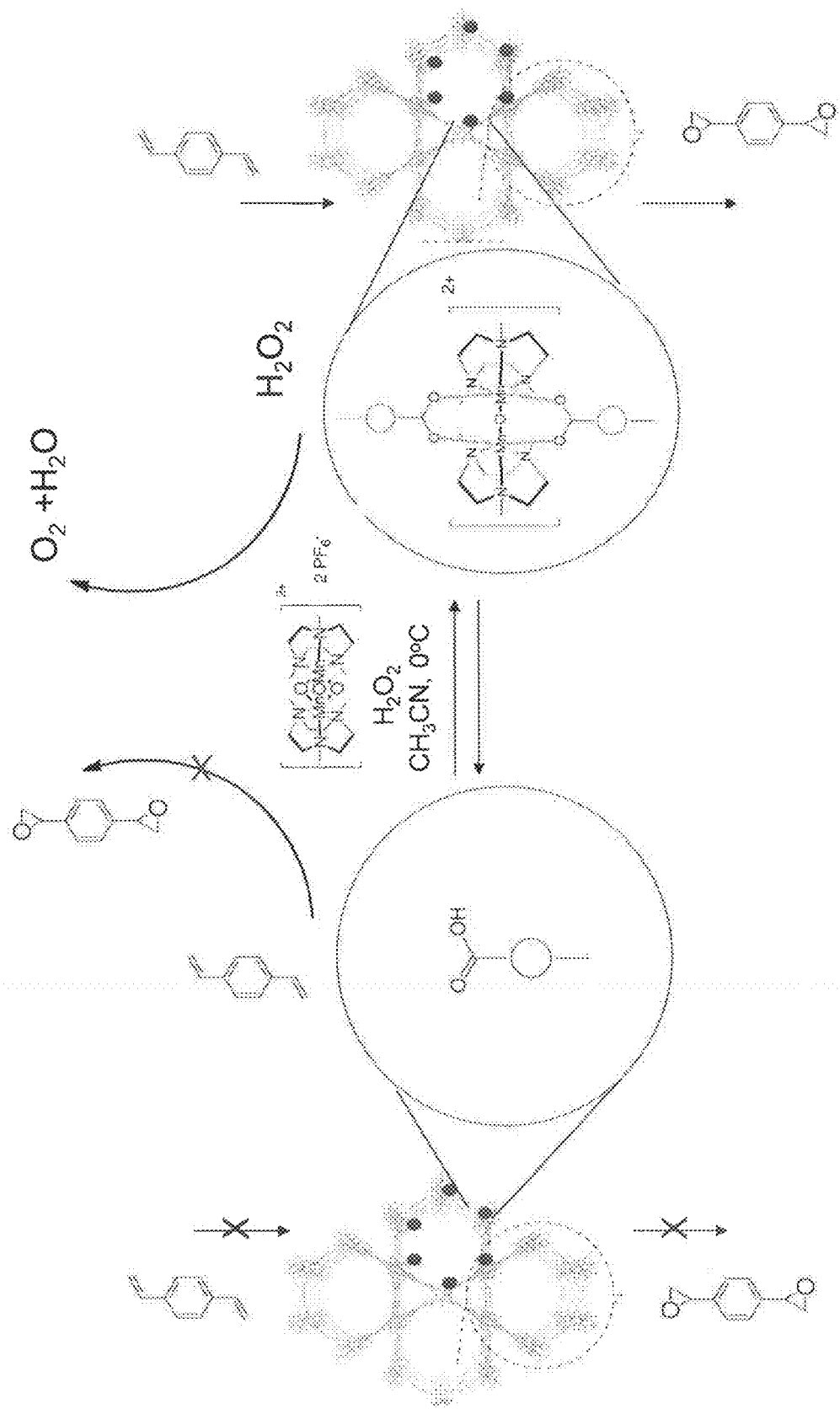
FIG. 3. Schematic illustration of epoxidation with NU-1000-A$^L$. (See, e.g., Examples 1-5.)
Figure 4A:
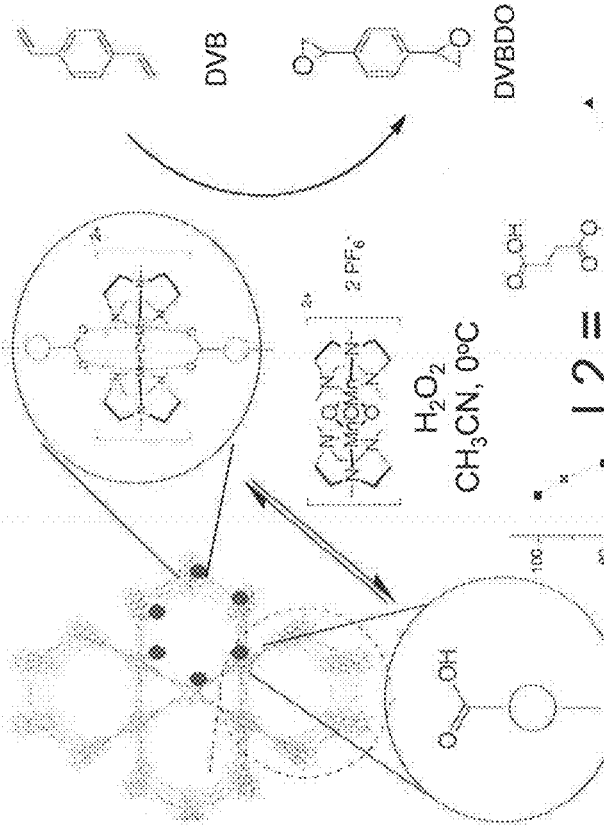
FIGS. 4A-D and FIG. 5.
Figure 4B:
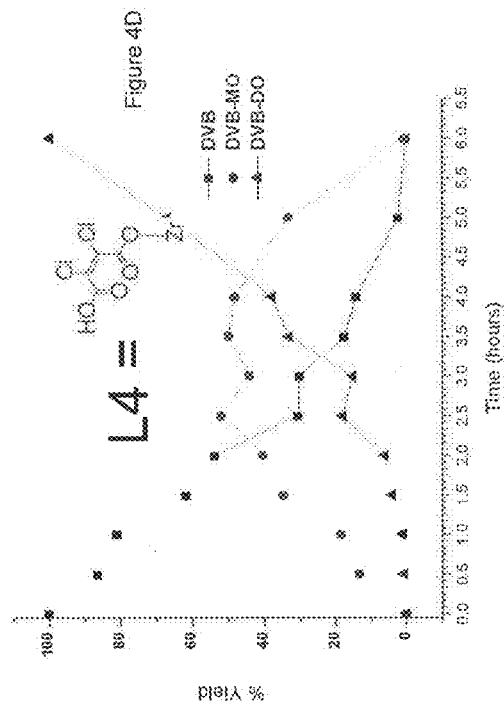
Figure 4C:
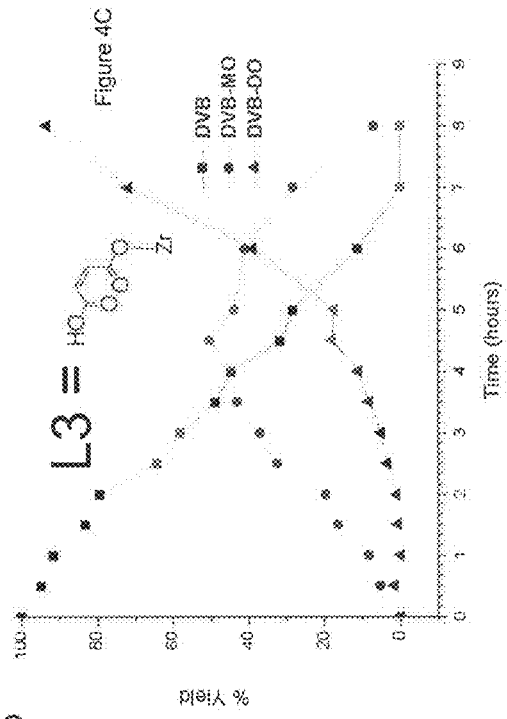
Figure 4D:
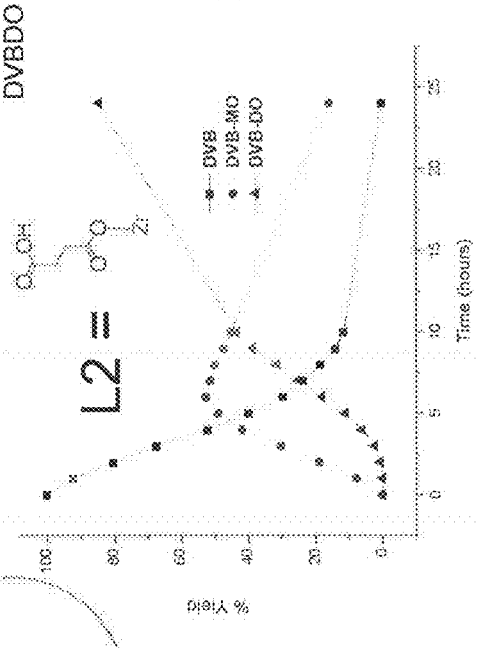

In one broad embodiment, the present invention includes a novel catalyst composition. The novel catalyst composition of the present invention includes at least two or more compounds including (a) a manganese-containing compound as a first compound; and (b) an acid functionalized ligand-containing compound such as a carboxylic acid functionalized metal organic framework (MOF) compound as a second compound.

The manganese (Mn)-containing compound, component (a), useful in the present invention catalyst composition can include, for example, one or a combination of two or more of the following compounds: a manganese triazacyclononane complex such as a (TMTACN)Mn complex; Mn-porphyrin; Mn-salen; Mn-Schiff base; or mixtures thereof.

In one embodiment, the Mn-containing compound of the catalyst composition of the present invention includes, for example, [Mn$_2$(TMTACN)$_2$($\mu$-O)$_3$](PF$_6$)$_2$.H$_2$O.

In general, component (b) of the catalyst composition of the present invention is based on a synthesized metal-organic framework (MOF) compound; and more specifically, component (b) includes a carboxylic acid functionalized MOF compound. The carboxylic acid functionalized MOF compound can include for example, one or a combination of two or more of the following compounds: a carboxylic acid-tethered Mn(TACN) MOF complex; [NU-1000-(A$^{L2}$)$_2$-(Mn$_2$(TMTACN)$_2$($\mu$-O)]; [NU-1000-(A$^{L3}$)$_2$-(Mn$_2$(TMTACN)$_2$($\mu$-O)]; [NU-1000-(A$^{L4}$)$_2$-(Mn$_2$(TMTACN)$_2$($\mu$-O)]; or mixtures thereof.

In one embodiment, the carboxylic acid functionalized MOF compound, component (b), useful in the present invention catalyst composition can be generated by reacting (i) a MOF compound and (ii) an acid ligand material that provides carboxylic acid functionalities to the MOF compound.

The MOF compound, component (i), useful for forming the carboxylic acid functionalized MOF compound can include for example, 2,6-naphthalenedicarboxylic acid (2,6-ndc); [3,2-b;2',3'-d]-thiophene dicarboxylate (DTTDC);

4',4''',4''''-methanetetrayltetrabiphenyl-1-4-carboxylic acid ($H_4MTBC$); and mixtures thereof.

For example, in one embodiment of the present invention, the MOF compound includes a compound having a molecular formula of: $Zr_6(OH)_8(TBAPy)_2$ wherein "TBAPy" is 1,3,6,8-tetrakis(p-benzoic acid)pyrene, herein designated as "NU-1000". The NU-1000 can be used as a building block for preparing other catalytic compositions.

In another embodiment of the present invention, for example, the MOF compound includes a compound having a molecular formula of: $Zr_6O_4(OH)_4(BTC)_2(HCOO)_6$, wherein "BTC" is benzene-1,3,5-tricarboxylic acid, herein designated as "MOF-808". The MOF-808 can also be used as a building block for preparing other catalytic compositions.

The acid ligand material, component (ii), useful for providing carboxylic acid functionalities to the MOF compound and thereby useful for forming the carboxylic acid functionalized MOF compound can include for example, succinic anhydride, maleic anhydride, 2,3-dichloro maleic anhydride, succinic acid, maleic acid, and mixtures thereof.

In one embodiment, the acid ligand material that provides carboxylic acid functionalities to the acid functionalized MOF compound can be derived from one or a combination of two or more acid anhydrides. The acid anhydrides include for example a compound selected from the group consisting essentially of succinic anhydride; maleic anhydride; 2,3-dichloromaleic anhydride; tetrafluorosuccinic anhydride; hexafluoroglutaric anhydride; and mixtures thereof.

In another embodiment, the acid ligand material that provides carboxylic acid functionalities to the acid functionalized MOF compound can be derived directly from one or more carboxylic acids. The carboxylic acids include for example a compound selected from the group consisting essentially of succinic acid; maleic acid; phosphonobenzoic acid; dichloromaleic acid and mixtures thereof.

As an illustration of the present invention, a carboxylic acid functionalized MOF compound can be prepared by admixing for example (i) NU-1000 and/or NU-808 and (ii) an acid ligand material such as for example a carboxylic acid. The above admixture results in the NU-1000 and/or MOF-808 being tethered to the acid ligand material such that a carboxylic acid functionalized MOF compound is formed. For example, when NU-1000 is used with an acid ligand material the carboxylic acid functionalized MOF compound formed can be designated herein as "NU-1000-$A^L$" and when the MOF-808 is used with an acid ligand material the carboxylic acid functionalized MOF compound formed can be designated herein as "MOF-808$A^L$".

Generally, the molar ratio of the MOF compound, component (i), to the acid ligand material, component (ii), used in the present invention to form the carboxylic acid functionalized MOF compound, may range for example, from 1 to about 1 in one embodiment, from about 1 to about 2 in another embodiment, from about 1 to about 4 in still another embodiment, from about 1 to about 5 in yet another embodiment.

The carboxylic acid functionalized MOF compound, once formed, such as NU-1000-$A^L$ or NU-808-$A^L$ can be combined with a manganese-containing compound to form the catalyst composition useful in the epoxidation process of the present invention. In this instance, the catalyst composition is a heterogeneous catalyst composition.

As an illustration of the present invention, when the manganese-containing compound is for example [$Mn_2$(TMTACN)$_2$(μ-O)$_3$](PF$_6$)$_2$.H$_2$O], one embodiment of the heterogeneous catalyst composition of the present invention can be designated as "[NU-1000-$A^L$+[$Mn_2$(TMTACN)$_2$(μ-O)$_3$](PF$_6$)$_2$H$_2$O]". Another embodiment of the heterogeneous catalyst composition of the present invention can be designated as "[MOF-808-$A^L$+[$Mn_2$(TMTACN)$_2$(μ-O)$_3$] (PF$_6$)$_2$.H$_2$O].

One advantage of aforementioned heterogeneous catalyst composition is that the catalyst composition is catalytically active towards the selective epoxidation of an olefin compound such as a divinylarene to an olefin oxide such as a divinylarene dioxide (e.g., a process for epoxidizing DVB to produce DVBDO). The epoxidation process of the present invention using the above catalyst composition beneficially mitigates complex purification processes, ensures recovery of the catalyst compositions, and makes production of olefin oxide products such as DVBDO feasible on an industrial scale.

Generally, the molar ratio of component (a) a manganese-containing compound to component (b) a carboxylic acid functionalized MOF compound used in the present invention to form the catalyst composition, may range for example, from 1 to about 2 in one embodiment.

The process for manufacturing the catalyst composition of the present invention includes the step of admixing (a) the above described manganese-containing compound and (b) the above described carboxylic acid functionalized MOF compound and any optional compounds/additives useful for various enduse applications. For example, the components for making the catalyst composition, and optionally any desirable additives, can be mixed or blended together, in known mixing equipment, in any order. The components, for example, may be added to a mixing vessel simultaneously (i.e., all at once) or consecutively (i.e., one at a time); and the components may be added intermittently in portions over time, or added continuously over time.

Another broad embodiment of the present invention includes a process for epoxidizing an olefin compound to form an epoxy compound using the above-described catalyst composition of the present invention. The process can be advantageously carried out under mild conditions as discussed herein.

In general, the epoxidation process of the present invention includes epoxidizing an olefin compound to form an epoxy compound including the step of reacting the following compounds: (A) at least one olefin compound; (B) at least one oxidant, and (C) at least one catalyst composition; wherein the catalyst composition includes the above-described catalyst composition, i.e., a catalyst composition of (a) a manganese-containing compound and (b) a carboxylic acid functionalized MOF compound.

The olefin compound, component (A), used in the present process includes any well-known olefin compound containing one or more olefin functionalities. Preferably, the olefin compound contains two or more (multi-) olefin functionalities. For example, the olefin compound containing multi-olefin functionalities can be an aromatic olefin compound. The olefin compound, component (A), used to prepare the epoxy compound product of the present invention includes any aromatic olefin compound containing one or more olefin functionalities. In a preferred embodiment, the aromatic olefin compound can be an aromatic multi-olefin compound containing two or more olefin groups. When using the above aromatic multi-olefin compound starting material in the present process, an aromatic multi-olefin oxide compound product can be prepared.

In one embodiment, the aromatic multi-olefin compound containing multi-olefin functionalities can be, for example, a divinylarene compound and the aromatic multi-olefin oxide compound product prepared can be, for example, a divinylarene dioxide compound. In one specific example, the divinylarene compound may be divinylbenzene and the divinylarene dioxide compound product prepared from the divinylbenzene can be a divinylbenzene dioxide compound.

In the divinylarene preferred embodiment, the source of divinylarene useful in the present invention may come from any known sources and particular to known processes for preparing divinylarenes. For example, divinylarenes can be prepared with salt or metal wastes from arenes and ethylene.

The divinylarene reactant useful in the process of the present invention may be illustrated by general chemical Structures (I)-IV as follows:

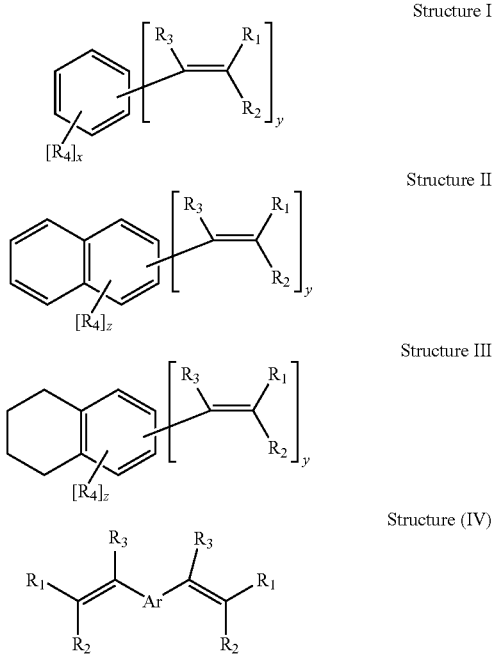

Structure I

Structure II

Structure III

Structure (IV)

In the above Structures (I), (II), (III) and (IV) of the divinylarene reactant of the present invention, each $R_1$, $R_2$, $R_3$ and $R_4$ individually may be hydrogen; an alkyl, cycloalkyl, an aryl or an aralkyl group, wherein the alkyl, cycloalkyl, aryl, and aralkyl groups may have from 1 to about 18 carbon atoms and preferably from 1 to 4 carbon atoms; or an oxidant-resistant group including for example a halogen, a nitro, an isocyanate, or an R'O group, wherein R' may be an alkyl, an aryl or an aralkyl group each individually having from 1 to about 18 carbon atoms and preferably from 1 to 4 carbon atoms; x may be an integer of 0 to 4; y may be an integer greater than or equal to 2; x+y may be an integer less than or equal to 6; z may be an integer of 0 to 6; z+y may be an integer less than or equal to 8; and Ar is an arene fragment including for example, 1,3-phenylene group.

In one embodiment of the present invention, the divinylarene useful in the present invention may comprise any substituted or unsubstituted arene nucleus bearing two vinyl (also referred to herein as "C=C bonds", "olefinic" or "ethylenic double bonds") groups in any ring position. The arene may include for example benzene, substituted benzenes, or (substituted) ring-annulated benzenes, and mixtures thereof. In one embodiment, divinylbenzene may be ortho, meta, or para isomers or any mixture thereof. Additional substituents may consist of oxidation-resistant groups including for example a saturated alkyl, or an aryl, wherein the saturated alkyl may have from 1 to about 18 carbon atoms and preferably from 1 to 4 carbon atoms, and wherein the aryl may have from 4 to about 18 carbon atoms and preferably from 6 to 10 carbon atoms; a halogen; a nitro, an isocyanate; or a R'O—wherein R' may be a saturated alkyl, an aryl, or an aralkyl each individually having from 1 to about 18 carbon atoms and preferably from 1 to 4 carbon atoms; or mixtures thereof. Ring-annulated benzenes may include for example naphthalene, tetrahydronaphthalene, and the like, and mixtures thereof.

In another embodiment, the divinylarene may contain quantities of substituted arenes. The amount and structure of the substituted arenes depend on the process used in the preparation of the divinylarene. For example, DVB prepared by the dehydrogenation of diethylbenzene (DEB) may optionally contain quantities of ethylvinylbenzene (EVB), naphthalene, polyethylbenzenes (e.g. diethylbenzene, triethylbenzene, tetraethylbenzene, pentaethylbenzene, diphenylethane, other aklylated benzenes, and higher molecular weight oils), free radical inhibitors, or mixtures thereof.

In one embodiment of the present invention, DVB may be epoxidized wherein DVB may optionally contain EVB. The DVB used can be a high purity DVB to make DVBDO with a very low amount of ethylvinylbenzene oxide (EVBO). "High purity" with reference to DVB herein means, for example, a DVB which contains greater than about 80% DVB in one embodiment, greater than about 90% DVB in another embodiment, and greater than about 95% DVB in yet another embodiment with the remainder being impurities or other compounds such as EVB.

In another embodiment, the process may provide, as a co-product, one or more divinylarene monoxides, alkyl-vinyl-arene monoxides, or mixtures thereof. When a monoxide product is produced as a co-product, the monoxide may be purified such that the purified monoxide product may have a purity of greater than about 50% in one embodiment, greater than about 80% in another embodiment, and greater than about 90% in yet another embodiment.

The divinylarene used in the process of the present invention may include for example divinylbenzene, divinylnaphthaiene, divinylbiphenyl, divinyldiphenylether; or mixtures thereof. In one preferred embodiment, the present invention uses divinylbenzene as the divinylarene reactant. In the above preferred embodiment using divinylbenzene as the divinylarene reactant, the divinylarene dioxide formed comprises divinylbenzene dioxide.

The concentration of the divinylarene used in the present invention may range generally from 0.01 mol/L (M) to about 10 M in one embodiment, from about 0.01 M to about 5 M in another embodiment, and from about 0.1 M to about 2 M in still another embodiment, based on the total mol and volume of the composition, In another preferred embodiment, the concentration of the divinylarene used in the present invention may range from about 0.2 M to about 1 M, from about 0.3 M to about 0.5 M in still another embodiment, and from about 0.3 M to about 0.4 M in yet another embodiment, based on the total weight of the composition.

The oxidizing agent or oxidant, component (B), useful in the present invention may include any oxygen transfer type oxidant well-known in the art. For example, the oxidant useful for preparing the epoxy compound of the present invention may include one or more of the oxidant compounds under the general classification of: (1) peroxo compounds or organic peroxides and (2) positive oxidation state halogen compounds; and (3) mixtures thereof.

Generally, examples of the peroxo compounds used as the oxidants in the process of the present invention include compounds with O—O linkages that are capable of losing one oxygen and forming an epoxide with a double bond. For example, the peroxo compounds used as the oxidants in the process of the present invention may include peroxocarboxylic acids, peroxosulfates, organic hydroperoxides, and mixtures thereof. More specifically, examples of the peroxo compounds may include hydrogen peroxide, Oxone®; potassium peroxomonsulfate or its ammonium or alkylammonium salts; meta-chloro-perbenzoic acid (mCPBA): peracetic acid; tert-butylhydroperoxide; cumene hydroperoxide; and mixtures thereof.

Generally, examples of the positive oxidation state halogen compounds used as the oxidants in the process of the present invention include compounds that contain halogens with an oxidation number of, for example, +1, +3, +5 or +7; and mixtures thereof. For example, compounds belonging to the group of positive oxidation state halogen compounds include for example, hypochlorites and hypobromites (+1); chlorites and bromites (+3); chlorates and brornates (+5): perchlorates, perbromates and periodates (+7); and mixtures thereof. More specifically, examples of the positive oxidation state halogen compounds include sodium periodate (+7); sodium hypochlorite (+1); iodosyl benzene (+3); iodosylmesitylene (+3); and mixtures thereof.

In one preferred embodiment, the oxidant used in the process of the present invention may be for example hydrogen peroxide ($H_2O_2$). $H_2O_2$ may be pre-manufactured or generated in-situ in the course of the reaction with the divinylarene, for example as disclosed in Edwards et al., J. Mater. Res., 22, (4) 831, 2007; or Hayashi et al., J. Catal., 178, 566, 1998. H2O2 may also be pre-manufactured using the anthraquinone/tetrahydroanthraquinone process with an appropriate hydrogenation catalyst such as palladium on alumina or Raney nickel such as described in U.S. Pat. No. 3,635,841.

One advantage of the present invention process is that a low amount of oxidant can be used in the present invention process compared to other known processes. For example, the amount of oxidant useful in the process of the present invention, measured in terms of moles of oxidant per double bond of the aromatic multi-olefin compound, generally can be less than about 8:1 in one embodiment. In another embodiment, for example when the oxidant is hydrogen peroxide and the divinyl compound is divinyl arene, the molar ratio of hydrogen peroxide per double bond of the divinylarene useful in the present invention can be from about 3:1 to about 8:1; from about 4:1 to about 8:1 in still another embodiment; and from about 7:1 to about 8:1 in yet another embodiment.

If less than the minimum ratio of $H_2O_2$ per double bond of the divinylarene (described above) is used, there may not be a sufficient amount of oxidant to epoxidize both of the double bonds in the divinylarene, i.e., a product that contains one epoxide group and one double bond on average. In addition, if less than the minimum ratio of $H_2O_2$ per double bond of the divinylarene is used, the resulting reaction product may be unstable, i.e., the reaction product may have an increase in viscosity, and ultimately may gel prior to further processing. If more than the maximum ratio of $H_2O_2$ per double bond of the divinylarene (described above) is used, the benefits of using the $H_2O_2$ oxidant in the reaction may no longer be economical; and use of more $H_2O_2$ oxidant may be wasteful.

The catalyst, component (C), useful in the epoxidation process of the present invention can be the catalyst composition described above, that is, a preferred embodiment of component (C) is the catalyst composition including a combination of (a) the above described manganese-containing compound and (b) the above described carboxylic acid functionalized MOF compound.

The catalyst useful in the present invention can be, for example, a catalyst composition that is soluble in the reaction mixture (i.e., a homogeneous catalyst), a catalyst composition that is insoluble in the reaction mixture (i.e., a heterogeneous catalyst), or a combination of soluble and insoluble materials (i.e., a homogeneous catalyst that is supported on a variety of carrier materials. For example, a homogeneous catalyst can be bound or immobilized on a variety of carrier materials to form a heterogeneous catalyst. The carrier material may include, for example, chitosan membranes; carbon xerogels; silicas such as SBA-15 and MCM 41; aluminas; MgO; clays; activated carbon; polystyrene; and mixtures thereof. In the present invention, one preferred embodiment of the catalyst used in the epoxidation process is a heterogeneous catalyst composition such as for example NU-1000-$A^{L4}$.

The amount of the catalyst composition used in the epoxidation process, measured in terms of moles of catalyst composition per double bond of the aromatic multi-olefin compound being epoxidized, generally can range from about 0.05 mol % to about 5 mol %, preferably from about 0.1 mol % to about 1 mol %, and more preferably from about 0.5 mol % to about 1 mol %.

One advantage of using the above catalyst composition in the process of the present invention is that the catalyst composition can be used for several cycles until the catalyst composition no longer functions as a catalyst. In other words, the catalyst composition of the present invention can be reused in the reaction process for several cycles before the catalyst requires to be reactivated, i.e., the catalyst's reaction activity continues for a long period of time before the catalyst deactivates as compared with other conventional catalysts. This can be measured in terms of the catalyst composition's "turnover number (TON)". The catalyst composition of the present invention can achieve a high TON. For example, the TON of the catalyst composition, when used at a catalyst loading of about 1 mol %, can range up to about 200 in one embodiment. In another embodiment, the TON of the catalyst composition, when used at a catalyst loading of about 0.5 mol %, can range up to about 400. In still another embodiment, the TON of the catalyst composition, when used at a catalyst loading of about 0.1 mol %, can range up to about 380. The TON can be determined by moles of double bond converted relative to moles of catalyst composition used.

An optional organic solvent, component (iv), can be used to prepare the epoxy compound of the present invention if desired and may include for example one or more of the following general class of compounds: hydrocarbons, halogenated hydrocarbons, aromatic solvents, and mixtures thereof. The optional solvent, when used in the epoxidation reaction mixture of the process of the present invention, may include for example any inert organic solvent that is inert to the oxidant and other components in the composition and under the reaction conditions. For example, the solvent may include halogenated alkanes such as dichloromethane; aromatics such as toluene; polar organic solvents such as dimethylformamide, acetonitrile, or ethers such as tetrahydrofuran; or ketones, such as acetone or methyl-ethyl ketone; or mixtures thereof.

Examples of suitable solvents useful in the process of the present invention may include, but not to be limited thereto, acetonitrile, dichloromethane, chloroform, dichlorobenzene, dichloroethane, toluene; acetone, MIBK, and mixtures thereof. Acetonitrile is an example of a preferred embodiment of the solvent that can be used in the epoxidation reaction process of the present invention.

Generally, the concentration of the optional solvent, when used in the present invention, may range for example, from 0 weight percent (wt %) to about 99 wt % in one embodiment, from about 20 wt % to about 99 wt % in another embodiment, from about 40 wt % to about 99 wt % in still another embodiment, from about 60 wt % to about 90 wt % in yet another embodiment, and from about 80 wt % to about 90 wt % in even still another embodiment, based on the weight of all the components in the composition.

An assortment of other optional additives known in the art may be added to the reaction mixture composition to prepare the epoxy compound of the present invention such as compounds that are normally used in epoxidation reactions known to those skilled in the art. For example, the optional components may include compounds that can be added to enhance (1) the properties of the final epoxy product such as surface tension modifiers or flow aids; (2) the reaction rate; (3) the selectivity of the reaction; and/or (4) the catalyst lifetime. The optional additives may include, for example, other resins, stabilizers, catalyst de-activators, and the like; and mixtures thereof.

The amount of the one or more several optional components or additives that can be used to prepare the epoxy compound, when used, may range generally from 0 wt 1% to about 99.9 wt % in one embodiment, from about 0.1 wt 2% to about 99.9 wt % in another embodiment, from about 1 wt % to about 99 wt % in still another embodiment, and from about 2 wt % to about 98 wt %, in yet another embodiment, base on the weight of all the components in the composition.

The process of the present invention for epoxidizing an aromatic olefin compound containing multi-olefin functionalities, such as a divinyl compound, to prepare an epoxy compound includes the step of reacting the above components after admixing or during the admixing of the compounds described above and adding any of the optional compounds/additives described above. Optional components known to the skilled artisan commonly used in an epoxidation reaction and other additives can be used for various enduse applications.

For example, the reaction components of the present invention described above, and optionally any desirable additives, can be mixed or blended together, in known mixing equipment, in any order. The reactants and optional additives, for example, may be added to the reaction mixture during the mixing or prior to the mixing to form a reaction mixture. In one embodiment, for example, the reaction components may be added to a reaction vessel all at once, added intermittently in portions over time, or added continuously over time. In another embodiment, the reaction mixture may exist in multiple phases.

Figure 5:
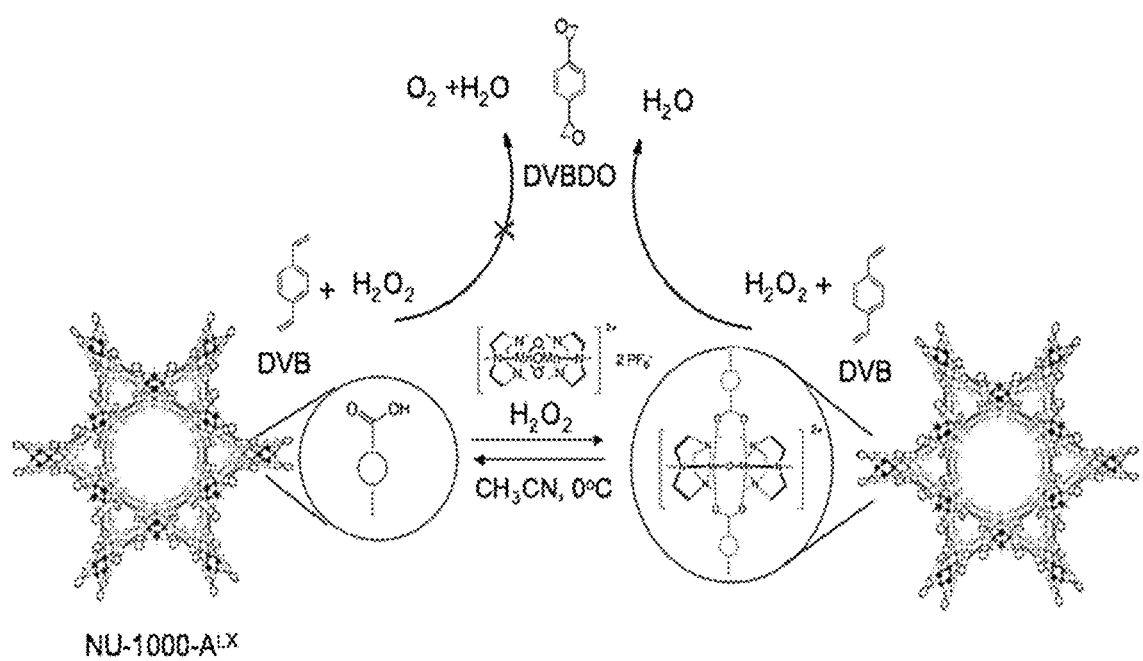

One specific preferred embodiment of the epoxidation process of the present invention includes epoxidizing an aromatic compound containing multi-olefin functionalities such as a divinylarene to form an aromatic epoxy compound containing multi-epoxide functionalities such as a divinylarene dioxide using the catalyst composition described above. This preferred specific embodiment of the present invention process can be illustrated, for example, by the reaction shown in the schematic illustration of FIG. 5, wherein a divinylbenzene is epoxidized using an oxidant and the catalyst composition of the present invention to form a divinylbenzene dioxide.

All the compounds of the reaction mixture are typically mixed and dispersed at a temperature enabling the formation of well mixed reaction mixture for use in the epoxidation reaction. For example, the mixing temperature of the components may be generally from about 0° C. to about 60° C. in one embodiment, and from about 0° C. to about 25° C. in another embodiment.

The mixing step of the present invention, and/or any of the steps thereof, may be a batch or a continuous process. The mixing equipment used in the process may be any vessel and ancillary equipment well known to those skilled in the art.

The process of the present invention includes the step of reacting the reaction mixture described above to form an epoxy compound. The reaction process may be a homogenous reaction or a heterogeneous reaction. The reaction in the present invention is a heterogeneous reaction based on the use of the heterogeneous catalyst composition described above. The reaction may be carried out at a predetermined temperature and for a predetermined period of time sufficient to epoxidize the aromatic multi-olefin compound and to form a resultant epoxy product having desirable properties for a particular application.

One of the advantages of the present invention is that the process of reacting the reaction mixture composition can be carried out under mild reaction conditions. For example, in one embodiment, the reaction may be carried out at various temperatures such as for example, generally from about −20° C. to about 100° C., from about 0° C. to about 80° C. in another embodiment, from about 0° C. to about 60° C. in still another embodiment, and from about 0° C. to about 25° C. in yet another embodiment.

The pressure of the reaction may be generally from about 10.13 kPa to about 1013 kPa (0.1 atmosphere [atm] to about 10 atm).

Generally, the reaction time for the reaction may be chosen to maximize olefin conversion and minimize epoxide decomposition. For example, the reaction time may be between about 1 hour (h) to about 24 h in one embodiment, between about 3 h to about 20 h in another embodiment, and between about 6 h to about 14 h in still another embodiment.

In one embodiment, the reaction of the present invention may be carried out in a single stage. In another embodiment, the reaction of the present invention may be carried out in multiple stages with separation of components between the multiple stages. Different flows patterns of reactant streams may be used. Also, the reactants may be added incrementally or all at once into a reactor. In addition, the reaction of the present invention, and/or any of the steps thereof, may be carried out batch-wise or continuously. The reaction equipment (reactor) used in the process may be any vessel and ancillary equipment well known to those skilled in the art.

For example, the present invention may include a process for epoxidizing an aromatic compound containing multi-olefin functionalities to form an epoxy compound including the steps of: (I) admixing the following compounds: (A) at least one olefin such as an aromatic olefin compound containing multi-olefin functionalities; (B) at least one oxidant such as a peroxo compound, and (C) a catalyst composition; wherein the catalyst composition comprises the catalyst composition described above; and then (II) adjusting the temperature of the mixture of step (I) to a reaction temperature of from about 0° C. to about 100° C. to react the compounds mixed in step (I).

In one preferred embodiment, the process of the present invention may include for example, a process for epoxidizing a divinyl compound such as a divinylarene to form an epoxy compound such as divinylarene dioxide. More preferably, the resulting epoxy compound produced by the above process can be for example divinylbenzene dioxide produced by epoxidizing divinylbenzene. In this preferred embodiment, the preparation of a divinylarene dioxide may be achieved for example by (1) adding to a reactor the following reactants: a divinylarene, a catalyst composition, and optionally an inert organic solvent; (2) contacting the reactants with an oxidant; and then (3) allowing the components in the reaction mixture to react under reaction conditions to produce the corresponding divinylarene dioxide.

After the reaction of the present invention, undesirable by-products; and any remaining catalyst composition, and solvent, may be removed to recover the divinylarene dioxide product. The resulting divinylarene dioxide reaction product can be isolated by any known means. Optionally, the divinylarene dioxide reaction product may be purified by well-known means in the art such as by chromatography, distillation, crystallization, and the like. In one preferred embodiment, the isolated divinylarene dioxide reaction product is purified by a distillation process.

The process of the present invention using the catalyst composition described above provides several advantages such as for example the process facilitates olefin dioxide formation in high yields (e.g., >70%) using low catalyst loadings (e.g., less than [<]1 mol %), while mitigating (1) the use of additives and/or (2) the generation of undesired byproduct waste.

One advantage of the present invention process over conventional processes includes the production of high yields of oxide product using the process of the present invention. With high yields of oxide product produced, the process of the present invention advantageously requires less recycle and produces less waste. For example, "high yield" of an olefin oxide product such as divinylarene dioxide produced by the process of the present invention may include generally a yield of greater than about 50% in one embodiment, from about 50% to about 100% in another embodiment, from about 60% to about 100% in still another embodiment; from about 70% to about 100% in yet another embodiment; from about 80% to about 100% in even still another embodiment, and from about 90% to about 100% in even yet another embodiment, based on olefin starting material.

Another advantage of the present invention process over conventional processes includes the production of high selectivities of oxide product by using the process of the present invention. For example, "high selectivity" of an olefin oxide product such as divinylarene dioxide produced by the process of the present invention may include generally a selectivity of greater than about 70% in one embodiment, from about 70% to about 100% in another embodiment; from about 80% to about 100% in still another embodiment; from about 85% to about 100% in yet another embodiment, and from about 90% to about 100% in even still another embodiment when running the reaction at a temperature of about 0° C., and based on the product formed.

Still another advantage of the present invention process is a process that can provide a substantially complete conversion of olefin groups to epoxy groups, i.e., a higher percentage of the olefin functionalities present in an olefin compound can be converted to epoxide groups than for an olefin compound processed by other conventional processes. In a preferred embodiment, it is desired to obtain 100% complete conversion of olefin groups to epoxy groups using the process of the present invention. However, for the purposes of the present invention, it is sufficient to achieve "substantially complete conversion" or something less than 100% conversion of olefin groups to epoxy groups in the present invention. "Substantially complete conversion" of the olefin groups to epoxy groups of an oxide product produced by the process of the present invention, herein means generally at least greater than about 80% of the olefin groups are converted to epoxy groups in one embodiment, from about 80% to about 100% in another embodiment; from about 90% to about 100% in still another embodiment; from about 95% to about 100% in yet another embodiment, and from about 98% to about 100% in even still another embodiment, based on the number of olefin groups in the olefin starting material. The above conversion percentages can be measured by quantitative GC analysis, or NMR analysis, using an appropriate internal standard as is known by one skilled in the art.

Yet another advantage of the present invention process is the capability of obtaining the above benefits of high yield, high selectivity, and high conversion at a low catalyst loading. For example, using the process of the present invention "low catalyst loading" may include generally a catalyst loading of less than about 2% in one embodiment, from about 0.1% to about 2% in another embodiment; and from about 0.5% to about 1% in still another embodiment, based on the total components in the reaction mixture.

In a conventional process, typical undesired waste in the form of byproducts can be produced during the epoxidation reaction of an olefin to form a desired olefin dioxide product. The byproducts can include, for example, ring-opening diols such as 1,1'-(1,4-phenylene)bis(ethane-1,2-diol). In the process of the present invention, the production of these unwanted byproducts can be minimized. For example, using the process of the present invention a "low amount of byproduct" may include generally a byproduct concentration of less than about 0.1 wt % in one embodiment, from about 0.01 wt % to about 0.1 wt % in another embodiment; from about 0.01 wt % to about 0.09 wt % in still another embodiment; from about 0.01 wt % to about 0.08 wt % in yet another embodiment, from about 0.01 wt % to about 0.07 wt % in even still another embodiment, and from about 0.01 wt % to about 0.06 wt % in even still another embodiment, based on the total components in the reaction mixture.

Yet another advantage of the present invention process over conventional processes relates to the speed of the epoxidation reaction, i.e., the process provides a faster epoxidation reaction. For example, high yields of oxide product can be obtained within a short period of time. F or example, the reaction time can be, generally, less than about 8 hours in one embodiment, from 4 hours to less than about 8 hours in another embodiment, from about 4 hours to about 7 hours in still another embodiment, from about 4 hours to about 6 hours in yet another embodiment; and from about 4 hours to about 5 hours in even still another embodiment.

Other advantages over the conventional processes relates to the use of additives. For example, the present invention process does not require additives such as acetone to achieve the high yields and other benefits described above.

In addition, the present invention is more efficient; and the present invention process can reduce and/or eliminate the need for extra equipment and extra separation/purification steps that can add to the complexity and cost of carrying the process on an industrial scale.

The epoxy compound product produced by the process of the present invention generally corresponds to the olefin compound starting material, component (A) described above. Preferably, the olefin compound starting material contains two or more (multi-) olefin functionalities. As aforementioned, in one preferred embodiment, an aromatic multi-olefin compound containing multi-olefin functionalities such as a divinylarene compound is used to prepare a aromatic multi-olefin oxide compound product such as a divinylarene dioxide compound. In a specific example, the divinylarene compound may be divinylbenzene and the divinylarene dioxide compound product prepared from the divinylbenzene can be a divinylbenzene dioxide compound.

The divinylarene dioxide product prepared by the process of the present invention may be illustrated generally by general chemical Structures (V)-(VIII) as follows:

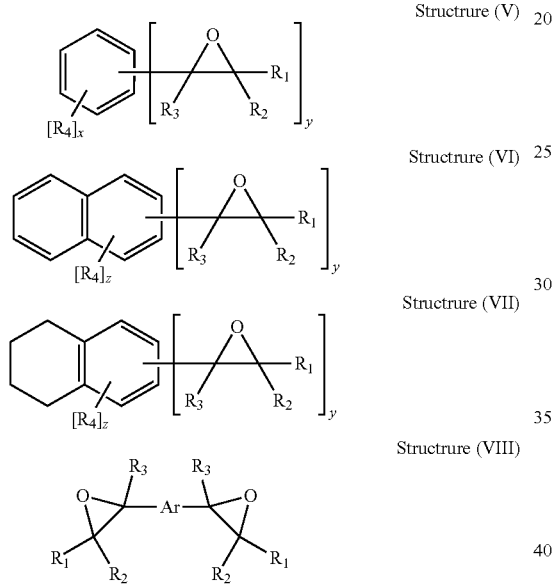

Structrure (V)

Structrure (VI)

Structrure (VII)

Structrure (VIII)

In the above Structures (V), (VI), (VII) and (VIII) of the divinylarene dioxide product of the present invention, each $R_1$, $R_2$, $R_3$ and $R_4$ individually may be hydrogen, an alkyl, cycloalkyl, an aryl or an aralkyl group, where the alkyl, cycloalkyl, aryl, and aralkyl groups may have from 1 to about 18 carbon atoms, preferably from 1 to 4 carbon atoms; or a oxidant-resistant group including for example a halogen, a nitro, an isocyanate, or an R'O group, wherein R' may be an alkyl, aryl or aralkyl group having from 1 to about 18 carbon atoms, preferably from 1 to 4 carbon atoms; x may be an integer of 0 to 4; y may be an integer greater than or equal to 2 x+y may be an integer less than or equal to 6; z may be an integer of 0 to 6, z+y may be an integer less than or equal to 8; and Ar is an arene fragment including for example, 1,3-phenylene group.

The divinylarene dioxide product produced by the process of the present invention may include for example alkyl-vinyl-arene monoxides depending on the presence of alkylvl-vinyvl-arene in the starting material. The structure of the divinylarene dioxide, and composition of structural isomers, is determined by the divinylarene feedstock used. The reaction to epoxidize the ethylenic bonds do not generally impact the isomer distribution of the reactants as they are converted.

In one embodiment of the present invention, the divinylarene dioxide produced by the process of the present invention may include for example divinylbenzene dioxide, divinvnylnaphthalene dioxide, divinylbiphenyl dioxide, divinyldiphenylether dioxide, and mixtures thereof.

In a preferred embodiment of the present invention, the divinylarene dioxide product produced can be for example DVBDO). Most preferably, the divinylarene dioxide product of the present invention includes, for example, a DVBDO as illustrated by the following chemical formula of Structure (IX):

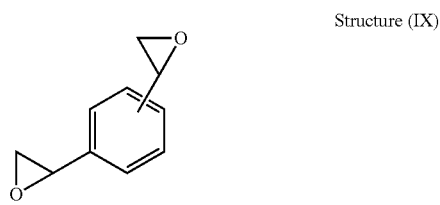

Structure (IX)

The chemical formula of the above DVBDO compound may be as follows: $C_{10}H_{10}O_2$; the molecular weight of the DVBDO is about 162.2; and the elemental analysis of the DVBDO is about: C, 74.06; H, 6.21; and O, 19.73 with an epoxide equivalent weight of about 81 g/mol.

Divinylarene dioxides, particularly those derived from divinylbenzene such as for example DVBDO, are class of diepoxides which have a relatively low liquid viscosity but a higher rigidity and crosslink density when cured than conventional epoxy resins.

Structure (X) below illustrates an embodiment of a preferred chemical structure of the DVBDO produced by the process of the present invention:

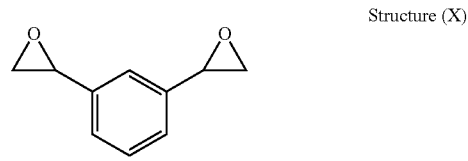 [SMILES: c1cc(C2CO2)cc(C2CO2)c1]

Structure (X)

Structure (XI) below illustrates another embodiment of a preferred chemical structure of the DVBDO produced by the process of the present invention:

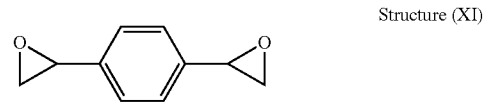 [SMILES: c1cc(C2CO2)ccc1C1CO1]

Structure (XI)

When DVBDO is prepared by the process of the present invention, it may be possible to obtain one of three possible isomers: ortho, meta, and para. Accordingly, the present invention includes a DVBDO illustrated by any one of the above structures individually or as a mixture thereof. Structures (X) and (XI) above show the meta (1,3-DVBDO) isomer of DVBDO and the para (1,4-DVBDO) isomer of DVBDO, respectively. The ortho isomer is rare; and usually DVBDO is mostly produced generally in a range of from about 9:1 to about 1:9 ratio of meta isomer (Structure (X)) to para isomer (Structure (XI)). The present invention preferably includes as one embodiment a range of from about 6:1 to about 1:6 ratio of Structure (X) to Structure (XI), and in other embodiments the ratio of Structure (X) to Structure (XI) may be from about 4:1 to about 1:4 or from about 2:1 to about 1:2.

The structure of the divinylarene dioxide, and composition of structural isomers, is determined by the divinylarene feedstock used. In one embodiment, divinylbenzene feedstock with a meta:para ratio of generally in a range of from about 9:1 to about 1:9 is preferred. In another embodiment, the divinylbenzene feedstock may be from about 6:1 to about 1:6; from about 4.1 to about 1:4 in yet another embodiment; from about 2.5:1 to about 1:2.5 in still another embodiment; or from about 1.5:1 to about 1:1.5 another embodiment. In a preferred embodiment, the meta:para ratio of the divinylbenzene and the divinylbenzene dioxide both may range from about 9:1 to about 1:9 ratio, and in another embodiment, the meta:para ratio of the divinylbenzene and the divinylbenzene dioxide both may range from about 2.5:1 to abut 1:2.5 ratio.

The feedstock may also contain impurities including, but not limited to, ethylvinylbenzene (EVB), naphthalene, polyethylbenzenes (e.g. diethylbenzene, triethylbenzene, tetraethylbenzene, pentaethylbenzene, diphenylethane, other aklylated benzenes, and higher molecular weight oils), free radical inhibitors, or mixtures thereof. The divinylbenzene content of the feed may be greater than 55% in one embodiment; greater than 63% in another embodiment; greater than 80% in still another embodiment; greater than 90% in still another embodiment; or greater than 95% in yet another embodiment. The amount of co-product EVBO that is produced and that must be separated to obtain higher purity DVBDO is determined by DVB feed stock composition. In one preferred embodiment, the divinylarene feed stock purity may be greater than about 80 percent.

In one embodiment, the process of the present invention may be particularly suited for the preparation of divinylbenzene dioxide, a low viscosity liquid epoxy resin. The divinylarene dioxides prepared by the process of the present invention, particularly divinylbenzene dioxide derived from divinylbenzene, are a class of diepoxides which have a relatively low liquid viscosity but a higher rigidity when cured than conventional epoxy resins. The viscosity of the divinylarene dioxides produced by the process of the present invention ranges generally from about 10 mP-s to about 100 mP-s; preferably, from about 10 mP-s to about 50 mP-s; and more preferably, from about 10 mP-s to about 25 mP-s at 25° C.

The utility of the divinylarene dioxides of the present invention may be advantageously their thermal stability to allow their formulation or processing at moderate temperatures (for example, at from about 100° C. to about 200° C.) for up to several hours (for example, for at least 2 hours) without oligomerization or homopolymerization. Oligomerization or homopolymerization during formulation or processing may be evident by a substantial increase in viscosity or gelling (crosslinking). The divinylarene dioxides of the present invention have sufficient thermal stability such that they do not experience a substantial increase in viscosity or gelling during formulation or processing at moderate temperatures.

The epoxy product produced by the process of the present invention, such as a divinylarene dioxide product, can be used in any application that conventional epoxy resins are used. For example, the epoxy product produced by the process of the present invention may be used as a component in a curable formulation or composition, which in turn, can be used to manufacture a cured thermoset product for various enduses such as coatings, films, adhesives, laminates, electronics, composites, and the like.

As an illustration of the present invention, in general, resin compositions based on the divinylarene dioxide products of the present invention may be useful for casting, potting, encapsulation, molding, and tooling. For example, the present invention may be used in electrical casting applications; for plastic molding and tooling; and for the fabrication of composites parts.

The diepoxide products prepared by the process of the present invention can be used to form various resin formulations or compositions. For example, the diepoxides produced by the process of the present invention such as DVBDO can serve as an epoxy component or as a reactive thinner in an epoxy thermoset formulation. A curable resin formulation or composition for manufacturing thermoset articles can include, for example, (1) the DVBDO epoxy product prepared as described above; and (2) at least one curing agent compound. Other optional additives known to the skilled artisan can be included in the curable composition such as for example a curing catalyst and other additives for various enduse applications. Epoxy formulations made from DVBDO, for example, are advantageous as intermediates for a variety of products in the fields of composites, coatings, molding compositions, and electronic packing.

EXAMPLES

The following examples and comparative examples further illustrate the present invention in detail but are not to be construed to limit the scope thereof.

Various terms and designations used in the following examples are explained herein below:

"GC" stands for gas chromatography.
"NMR" stands for nuclear magnetic resonance.
"DVB" stands for divinylbenzene.
"DVBDO" stands for divinylbenzene dioxide.
"DVBMO" stands for divinylbenzene monoxide.
"EVBO" stands for ethylvinylbenzene oxide.
"EVB" stands for ethylvinylbenzene.
"TMTACN" stands for 1,4,7-trimethyl-1,4,7-triazacyclononane.
"GC-FID" stands for gas chromatography-flame ionization detector.
"GC-MS" stands for gas chromatography-mass spectrometry.

Materials.

The various materials used in the following examples are explained herein below:

$[Mn_2(TMTACN)_2(\mu-O)_3](PF_6)_2 \cdot H_2O$ was prepared following the procedure reported in the following reference: Schoenfeldt et al., *Chem. Commun.*, 2010, 46, 1640-1642; incorporated herein by reference.

"TBAPy" stands for 1,3,6,8-tetrakis(p-benzoic acid) pyrene.

$H_4TBAPy$ was prepared following the procedure reported in the following reference: Mondloch, et al., *J. Am. Chem. Soc.*, 2013, 135, 10294-10297; incorporated herein by reference.

"NU-1000" is $Zr_6(OH)_8(TBAPy)_2$.

NU-1000 was prepared following the procedure reported in the following reference: Mondloch, et al., *J. Am. Chem. Soc.*, 2013, 135, 10294-10297; incorporated herein by reference.

NU-1000 was activated using a slightly modified method from that reported by Feng et al., *Angew. Chem. Int. Ed.*, 2013, 135, 10307-10310; incorporated herein by reference.

All the gases used for the adsorption/desorption are ultra-high purity grade 5 and are commercially available from Airgas Specialty Gases.

Butyric acid, crotonic acid, succinic anhydride, maleic anhydride, 2,3-dichloromaleic anhydride, chlorobenzene, anhydrous acetonitrile, and hydrogen peroxide ($H_2O_2$ (30%, w/w in $H_2O$) magnesium sulfate ($MgSO_4$), and silver (Ag) powder are commercially available from the Aldrich Chemical Company.

DVBMO, EVBO, and DVBDO are available from The Dow Chemical Company.

Deuterated solvents are commercially available from Cambridge Isotope Laboratories.

Methods.

The following standard analytical equipments and methods are used in the Examples:

NU-1000 modification and epoxidation reactions were performed in 2-5 mL microwave vials commercially available from Biotage, LLC.

$^1$H NMR spectra were recorded on a Bruker Avance 500 MHz (499.4 MHz for 1H, 125.8 MHz for $^{13}$C) spectrometer from Bruker Biospin Corp.

Fourier-transformed infrared (FTIR) spectroscopy was performed on a Thermo Nicolet Nexus 879 FTIR spectrometer from Thermo Scientific using a smart diffuse reflectance accessory.

Thermogravimetric analysis (TGA) data were obtained with a Mettler-Toledo TGA/DSC1 Star thermal analyzer from Mettler-Toledo.

UV-vis spectra were obtained in $CH_3CN$ on a Varian Cary 500 spectrophotometer.

All nitrogen ($N_2$) adsorption and desorption measurements were performed on a Micromeritics Tristar 3020 system from Micromeretics.

Pore size distributions were calculated from the adsorption-desorption isotherms by density functional theory (DFT).

GC-MS analysis was carried out on a Shimadzu QP-2010 GC-MS equipped with an MS detector and a Phenomenex ZB-624 column (30 m×250 mm diameter×1.4 mm film thickness). Analysis parameters were as followed: initial temperature=60° C., initial time=1 minutes, ramp=10° C./min, ramp to 150° C., then a slow ramp=2° C./min, ramp to 180° C., hold for 5 min, final ramp=10° C./min to 250° C., final time=15 minutes, total flow=78 mL/min, purge flow: 3 mL/min. Elution times (min)=18.5 (DVBMO meta), 18.9 (DVBMO para), 16.8 (EVBO meta), 17.2 (EVBO para), 27.8 (DVBDO meta), 28.4 (DVBDO para). Plots of alkene and product yield vs. time for the epoxidation of DVB were derived from areas the GC-FID traces associated only with DVB, DVBMO, and DVBDO generated using the Agilent ChemStation software.

GC-FID analysis was carried out on an Agilent Technologies 7820A GC system equipped with a flame ionization detector (FID) and an Agilent J&W GC HP-5 capillary column (30 m×320 mm×0.25 mm film thickness). Analysis parameters were as followed: initial temperature=75° C., initial time=5 minutes, ramp=6° C./min, final temperature=200° C., final time=5 minutes, flow rate=6.5 mL/min. Elution times (min)=4.814 (DVBmeta), 5.128 min (DVBpara), 4.026 (EVB meta), 4.201 (EVBpara), 9.730 (DVBMO meta), 9.945 (DVBMOpara), 8.947 (EVBO meta), 9.170 (EVBOpara), 14.047 (DVBDO meta), 14.191 (DVBDO para), 11.435, and 11.626 (benzaldehyde derivatives). The amount/area ratios for each of the components and the standard (chlorobenzene) were generated using the Agilent ChemStation software.

Synthesis Example I—Making NU-1000

NU-1000 was synthesized following the procedure reported in the following reference: Mondloch, et al., *J. Am. Chem. Soc.,* 2013, 135, 10294-10297; incorporated herein by reference.

In a 6-dram vial, $ZrCl_4$ (70 mg, 0.30 mmol), benzoic acid (2.7 g, 22 mmol), and dimethylformamide (DMF) (8 mL) were combined and the resulting mixture was ultrasonically dissolved into a clear solution. The vial was capped and incubated in an oven at 80° C. for 1 hour (h). After cooling down to room temperature (about 25° C.), $H_4$TBAPy (40 mg, 0.06 mmol) was added to the vial and the resulting mixture was sonicated for 20 minutes (min) to afford a yellow suspension. The vial was recapped and heated in an oven at 120° C. for 48 h. After cooling down the resulting solution in the vial to room temperature, a yellow polycrystalline material, un-activated NU-1000 was isolated by filtration and washed with DMF.

NU-1000 was activated using the general activation procedure below which is a modified procedure from the method reported in the following reference: Feng et al. Angew. Chem. Int. Ed., 2013, 135, 10307-10310; incorporated herein by reference.

The yellow polycrystalline material in a solution of DMF (12 mL) and 8 M aqueous HCl (0.5 mL) was heated in an oven at 100° C. for 24 h. After cooling to room temperature, the liquid in the vial was removed from the solids and the resultant material was washed twice with DMF to remove HCl impurities. The resultant solid residue was subsequently washed twice with acetone (10 mL) and soaked in acetone (15 mL) for additional 12 h. The washed material, activated NU-1000, was filtered, briefly dried on a filter paper and then heated at 120° C. under vacuum for 12 h. Successful activation was confirmed by disappearance of proton peaks associated with benzoic acid by solution-state 1H NMR spectroscopy.

Synthesis Example II—Making NU-1000-$A^{L2}$

The NU-1000 material prepared in Synthesis Example I above was used in this synthesis example to prepare an acid ligand modified NU-1000 material, herein designated as "NU-1000-$A^{L2}$".

The activated NU-1000 material from Synthesis Example I (approximately [~]42 mg, 0.02 mmol) was placed into a 2-5 mL microwave vial. A solution of succinic anhydride (~9.7 mg, 0.1 mmol, 5 equivalents [equiv]) pre-dissolved in acetonitrile ($CH_3CN$) (2 mL) was added to the vial. The vial was capped and then subsequently heated at 80° C. for 24 h without stirring. The resulting reaction mixture was allowed to cool to room temperature and then decanted to remove the solvent from the solids. To the resultant yellow microcrystalline solid was added anhydrous $CH_3CN$ (3 mL); and the resulting mixture was left standing for ~12 h. Thereafter, the mixture was decanted to remove the solvent from the solids and then new solvent was added to the mixture.

The above solvent exchange process was repeated three times over a 36 h period. At the end of the 36 h period, an acid ligand modified NU-1000 material, "NU-1000-$A^{L2}$", was formed. Then the NU-1000-$A^{L2}$ was collected via filtration over a Buchner funnel, washed with $CH_3CN$, briefly air-dried, and then dried overnight under vacuum at 120° C. to afford NU-1000-$A^{L2}$ as a yellow microcrystalline solid.

Synthesis Example III—Making NU-1000-A$^{L3}$

The general procedure described in Synthesis Example II above was used in this synthesis example with a different anhydride material as follows:

The NU-1000 material from Synthesis Example I (~48 mg, 0.02 mmol) was placed into a 2-5 mL microwave vial. A solution of maleic anhydride (~10.9 mg, 0.11 mmol, 5 equiv) pre-dissolved in CH$_3$CN (2 mL) was added to the vial. The vial was capped and then subsequently heated at 80° C. for 24 h without stirring. The resulting reaction mixture was allowed to cool to room temperature and the solvent was decanted. To the resultant yellow microcrystalline solid was added anhydrous CH$_3$CN (3 mL); and the resulting mixture was left standing for ~12 h. Thereafter, the mixture was decanted to remove the solvent from the solids and then new solvent was added to the mixture.

The above solvent exchange process was repeated three times over a 36 h period. At the end of the 36 h period, an acid ligand modified NU-1000 material, herein designated as "NU-1000-A$^{L3}$", was collected via filtration over a Büchner funnel, washed with CH$_3$CN, briefly air-dried, and then dried overnight under vacuum at 120° C. to afford NU-1000-A$^{L3}$ as a yellow microcrystalline solid.

Synthesis Example IV—Making NU-1000-A$^{L4}$

The general procedure described in Synthesis Example II above was used in this synthesis example with a different anhydride material as follows:

The NU-1000 material from Synthesis Example I (~45 mg, 0.02 mmol) was placed into a 2-5 mL microwave vial. A solution of 2,3-dichloromaleic anhydride (~17.4 mg, 0.1 mmol, 5 equiv) pre-dissolved in CH$_3$CN (2 mL) was added to the vial. The vial was capped and then subsequently heated at 80° C. for 24 h without stirring. The resulting reaction mixture was allowed to cool to room temperature and the solvent was decanted. To the resultant yellow microcrystalline solid was added anhydrous CH$_3$CN (3 mL); and the resulting mixture was left standing for ~12 h. Thereafter, the mixture was decanted to remove the solvent from the solids and then new solvent was added to the mixture.

The above solvent exchange process was repeated three times over a 36 h period. At the end of the 36 h period, an acid ligand modified NU-1000 material, herein designated as "NU-1000-A$^{L4}$", was collected via filtration over a Büchner funnel, washed with CH$_3$CN, briefly air-dried, and then dried overnight under vacuum at 120° C. to afford NU-1000-A$^{L4}$ as a yellow microcrystalline solid.

The chlorine wt % of the isolated product was determined by Neutron Activation Analysis (NAA) and found to be 6.46 wt % which is close to the predicted value of 5.68 wt %.

Comparative Example (Comp. Ex.) A—Epoxidation of DVB with NU-1000

The NU-1000 material from Synthesis Example I (~9.5 mg, 0.004 mmol) was placed into a 2-5 mL microwave vial equipped with a magnetic stir bar. Anhydrous CH$_3$CN (1 mL), [Mn$_2$(TMTACN)$_2$(μ-O)$_3$](PF$_6$)$_2$.H$_2$O (~1.75 mg, 0.002 mmol) pre-dissolved in CH$_3$CN (200 μL), chlorobenzene (45 μL, 0.45 mmol), and DVB (63.26 μL, 0.45 mmol) were added to the vial. The solution in the vial was stirred and when the solution equilibrated to a temperature of ~0° C. after 20 min using an ice bath, aqueous H$_2$O$_2$ (30 wt %, 37.2 μL, 0.82 equiv, 0.37 mmol) was added to the stirred solution through a micropipette. The vial was subsequently capped and kept at ~0° C. throughout the duration of the reaction.

At each hour, the vial was uncapped and aliquots of the reaction mixture (30 μL) were taken for analysis. Aqueous H$_2$O$_2$ (30 wt %, 37.2 μL, 0.82 equiv, 0.37 mmol) was added through a micropipette before the vial was closed again. (At the end of the reaction, a total of 372 μL total, 8.2 equiv, 3.7 mmol have been added). Each of the aliquots was passed through a glass pipette plug that was prepacked with glass wool, MgSO$_4$ (~5 mg), and Ag powder (~5 mg). The plug was then rinsed with anhydrous CH$_3$CN (1 mL) and the combined organic was monitored by GC-FID or GC-MS using the aforementioned procedure described in the Methods section. The results of this Comparative Example A are shown in Table I.

Comparative Example B—Epoxidation of DVB with Butyric Acid

Anhydrous CH$_3$CN (1 mL), [Mn$_2$(TMTACN)$_2$(μ-O)$_3$](PF$_6$)$_2$.H$_2$O (~1.75 mg, 0.002 mmol) pre-dissolved in CH$_3$CN (200 μL), butyric acid (~40.7 μL of a 0.108 M solution in CH$_3$CN, 0.004 mmol), chlorobenzene (45 μL, 0.45 mmol), and DVB (63.26 μL, 0.45 mmol) were added into a 2-5 mL microwave vial equipped with a magnetic stir bar. Upon the resultant solution equilibrating to ~0° C. for 20 min using an ice bath, to the stirred solution was added aqueous H$_2$O$_2$ (30 wt %, 37.2 μL, 0.82 equiv, 0.37 mmol) through a micropipette. The vial was subsequently capped and kept at ~0° C. throughout the duration of the reaction.

At each hour, the vial was uncapped and aliquots of the reaction mixture (30 μL) were taken for analysis. Aqueous H$_2$O$_2$ (30 wt %, 37.2 μL, 0.82 equiv, 0.37 mmol) was added through a micropipette before the vial was closed again. (At the end of the reaction, a total of 372 μL total, 8.2 equiv, 3.7 mmol have been added). Each of the aliquots was passed through a glass pipette plug that was prepacked with glass wool, MgSO$_4$ (~5 mg), and Ag powder (~5 mg). The plug was then rinsed with anhydrous CH$_3$CN (1 mL) and the combined organic was monitored by GC-FID or GC-MS using the aforementioned procedure described in the Methods section. The results of this Comparative Example B are shown in Table I.

Comparative Example C—Epoxidation of DVB with Crotonic Acid

Anhydrous CH$_3$CN (1 mL), [Mn$_2$(TMTACN)$_2$(μ-O)$_3$](PF$_6$)$_2$.H$_2$O (~1.75 mg, 0.0022 mmol) pre-dissolved in CH$_3$CN (200 μL), crotonic acid (~40.7 μL of 0.108 M solution in CH$_3$CN, 0.004 mmol), chlorobenzene (45 μL, 0.45 mmol), and DVB (63.26 μL, 0.45 mmol) were added into a 2-5 mL microwave vial equipped with a magnetic stir bar. Upon the resultant solution equilibrating to ~0° C. for 20 min using an ice bath, to the stirred solution was added aqueous H$_2$O$_2$ (30 wt %, 37.2 μL, 0.82 equiv, 0.37 mmol) through a micropipette. The vial was subsequently capped and kept at ~0° C. throughout the duration of the reaction.

At each hour, the vial was uncapped and aliquots of the reaction mixture (30 μL) were taken for analysis. Aqueous H$_2$O$_2$ (30 wt %, 37.2 μL, 0.82 equiv, 0.37 mmol) was added through a micropipette before the vial was closed again. (At the end of the reaction, a total of 372 μL total, 8.2 equiv, 3.7 mmol have been added). Each of the aliquots was passed through a glass pipette plug that was prepacked with glass wool, MgSO$_4$ (~5 mg), and Ag powder (~5 mg). The plug was then rinsed with anhydrous $CH_3CN$ (1 mL) and the combined organic was monitored by GC-FID or GC-MS using the aforementioned procedure described in the Methods section. The results of this Comparative Example C are shown in Table I.

Example (Ex.) 1—Epoxidation of DVB with NU-1000-A$^{L2}$

The NU-1000-A$^{L2}$ material from Synthesis Example II (~10.1 mg, 0.004 mmol) was placed into a 2-5 mL microwave vial equipped with a magnetic stir bar. Anhydrous $CH_3CN$ (1 mL), $[Mn_2(TMTACN)_2(\mu-O)_3](PF_6)_2 \cdot H_2O$ (~1.75 mg, 0.002 mmol) pre-dissolved in $CH_3CN$ (200 μL), chlorobenzene (45 μL, 0.45 mmol), and DVB (63.26 μL, 0.45 mmol) were added. Upon equilibrating to ~0° C. for 20 min using an ice bath, the stirred solution was added aqueous $H_2O_2$ (30 wt %, 37.2 μL, 0.82 equiv, 0.37 mmol) through a micropipette. The vial was subsequently capped and kept at ~0° C. throughout the duration of the reaction.

At each hour, the vial was uncapped and aliquots of the reaction mixture (30 μL) were taken for analysis. Aqueous $H_2O_2$ (30 wt %, 37.2 μL, 0.82 equiv, 0.37 mmol) was added through a micropipette before the vial was closed again. (At the end of the reaction, a total of 372 μL total, 8.2 equiv, 3.7 mmol have been added). Each of the aliquots was passed through a glass pipette plug that was prepacked with glass wool, $MgSO_4$ (~5 mg), and Ag powder (~5 mg). The plug was then rinsed with anhydrous $CH_3CN$ (1 mL) and the combined organic was monitored by GC-FID or GC-MS using the aforementioned procedure described in the Methods section. The results of this Example 1 are shown in Table I.

Example 2—Epoxidation of DVB with NU-1000-A$^{L3}$

The NU-1000-A$^{L3}$ material from Synthesis Example III (~10.1 mg, 0.004 mmol) was placed into a 2-5 mL microwave vial equipped with a magnetic stir bar. Anhydrous $CH_3CN$ (1 mL), $[Mn_2(TMTACN)_2(\mu-O)_3](PF_6)_2 \cdot H_2O$ (~1.75 mg, 0.002 mmol) pre-dissolved in $CH_3CN$ (200 μL), chlorobenzene (45 μL, 0.45 mmol), and DVB (63.26 μL, 0.45 mmol) were added. Upon equilibrating to ~0° C. for 20 min using an ice bath, the stirred solution was added aqueous $H_2O_2$ (30 wt %, 37.2 μL, 0.82 equiv 0.37 mmol) through a micropipette. The vial was subsequently capped and kept at ~0° C. throughout the duration of the reaction.

At each hour, the vial was uncapped and aliquots of the reaction mixture (30 μL) were taken for analysis. Aqueous $H_2O_2$ (30 wt %, 37.2 μL, 0.82 equiv, 0.37 mmol) was added through a micropipette before the vial was closed again. (At the end of the reaction, a total of 372 μL total, 8.2 equiv, 3.7 mmol have been added). Each of the aliquots was passed through a glass pipette plug that was prepacked with glass wool, $MgSO^4$ (~5 mg), and Ag powder (~5 mg). The plug was then rinsed with anhydrous $CH_3CN$ (1 mL) and the combined organic was monitored by GC-FID or GC-MS using the aforementioned procedure described in the Methods section. The results of this Example 2 are shown in Table I.

Example 3—Epoxidation of DVB with NU-1000-A$^{L4}$

The NU-1000-A$^{L4}$ material from Synthesis Example IV (~10.5 mg, 0.004 mmol) was placed into a 2-5 mL microwave vial equipped with a magnetic stir bar. Anhydrous $CH_3CN$ (1 mL), $[Mn_2(TMTACN)_2(\mu-O)_3](PF_6)_2 \cdot H_2O$ (~1.75 mg, 0.002 mmol) pre-dissolved in $CH_3CN$ (200 μL), chlorobenzene (45 μL, 0.45 mmol), and DVB (63.26 μL, 0.45 mmol) were added. Upon the resultant stirred solution equilibrating to ~0° C. for 20 min using an ice bath, to the stirred solution was added aqueous $H_2O_2$ (30 wt %, 37.2 μL, 0.82 equiv, 0.37 mmol) through a micropipette. The vial was subsequently capped and kept at ~0° C. throughout the duration of the reaction.

At each hour, the vial was uncapped and aliquots of the reaction mixture (30 μL) were taken for analysis. Aqueous $H_2O_2$ (30 wt %, 37.2 μL, 0.82 equiv, 0.37 mmol) was added through a micropipette before the vial was closed again. (At the end of the reaction, a total of 260 μL total, 5.7 equiv, 2.5 mmol have been added). Each of the aliquots was passed through a glass pipette plug that was prepacked with glass wool, $MgSO_4$ (~5 mg), and Ag powder (~5 mg). The plug was then rinsed with anhydrous $CH_3CN$ (1 mL) and the combined organic was monitored by GC-FID or GC-MS using the aforementioned procedure described in the Methods section. The results of this Example 3 are shown in Table I.

Example 4—Epoxidation of DVB with NU-1000-A$^{L4}$

The NU-1000-A$^{L4}$ material from Synthesis Example IV (~10.5 mg, 0.004 mmol) was placed into a 2-5 mL microwave vial equipped with a magnetic stir bar. Anhydrous $CH_3CN$ (1 mL), $[Mn_2(TMTACN)_2(\mu-O)_3](PF_6)_2 \cdot H_2O$ (~1.75 mg, 0.002 mmol) pre-dissolved in $CH_3CN$ (200 μL), chlorobenzene (45 μL, 0.45 mmol), and DVB (63.26 μL, 0.45 mmol) were added. Upon equilibrating to ~0° C. for 20 min using an ice bath, the stirred solution was added aqueous $H_2O_2$ (30 wt %, 74.4 μL, 1.64 equiv, 0.73 mmol) through a micropipette. The vial was subsequently capped and kept at ~0° C. throughout the duration of the reaction.

At each hour, the vial was uncapped and aliquots of the reaction mixture (30 μL) were taken for analysis. Aqueous $H_2O_2$ (30 wt %, 74.4 μL, 1.64 equiv, 0.73 mmol) was added through a micropipette before the vial was closed again. (At the end of the reaction, a total of 372 μL total, 8.2 equiv, 3.7 mmol have been added). Each of the aliquots was passed through a glass pipette plug that was prepacked with glass wool, $MgSO_4$ (~5 mg), and Ag powder (~5 mg). The plug was then rinsed with anhydrous $CH_3CN$ (1 mL) and the combined organic was monitored by GC-FID or GC-MS using the aforementioned procedure described in the Methods section. The results of this Example 4 are shown in Table I.

Example 5—Epoxidation of DVB with NU-1000-A$^{L4}$ at 25° C.

The NU-1000-A$^{L4}$ material from Synthesis Example IV (~10.5 mg, 0.004 mmol) was placed into a 2-5 mL microwave vial equipped with a magnetic stir bar. Anhydrous $CH_3CN$ (1 mL), $[Mn_2(TMTACN)_2(\mu-O)_3](PF_6)_2 \cdot H_2O$ (~1.75 mg, 0.002 mmol) pre-dissolved in $CH_3CN$ (200 μL), chlorobenzene (45 μL, 0.45 mmol), and DVB (63.26 μL, 0.45 mmol) were added. Upon equilibrating to ~0° C. for 20 min using an ice bath, the stirred solution was added aqueous $H_2O_2$ (30 wt %, 74.4 μL, 1.64 equiv, 0.73 mmol) through a micropipette. The vial was subsequently capped and kept at ~25° C. throughout the duration of the reaction.

At each hour, the vial was uncapped and aliquots of the reaction mixture (30 µL) were taken for analysis. Aqueous $H_2O_2$ (30 wt %, 74.4 µL, 1.64 equiv, 0.73 mmol) was added through a micropipette before the vial was closed again. (At the end of the reaction, a total of 372 µL, 8.2 equiv, 3.7 mmol have been added). Each of the aliquots was passed through a glass pipette plug that was prepacked with glass wool, $MgSO_4$ (~5 mg), and Ag powder (~5 mg). The plug was then rinsed with anhydrous $CH_3CN$ (1 mL) and the combined organic was monitored by GC-FID or GC-MS using the aforementioned procedure described in the Methods section. The results of this Example 5 are shown in Table I.

Example 6—Reuse of NU-1000-$A^{L4}$ for Epoxidation of DVB-$2^{nd}$ Cycle

After epoxidation in Example 4, the supernatant solution was decanted from the 2-5 mL microwave vial. To the yellow microcrystalline solid, NU-1000-$A^{L4}$, that remains in the vial was added anhydrous $CH_3CN$ (3 mL). The resultant mixture was left standing for ~12 h. Thereafter, the supernatant solution was decanted from the vial and then new solvent, $CH_3CN$ (3 mL), was added to the vial. This solvent exchange process was repeated three times over a 48 h period.

NU-1000-$A^{L4}$ was collected via filtration over a Büchner funnel, washed with $CH_3CN$, briefly air-dried, and then dried overnight under vacuum at 120° C. NU-1000-$A^{L4}$ (~10.5 mg, 0.004 mmol) was placed into a 2-5 mL microwave vial equipped with a magnetic stir bar. Anhydrous $CH_3CN$ (1 mL), $[Mn_2(TMTACN)_2(\mu-O)_3](PF_6)_2 \cdot H_2O$ (~1.75 mg, 0.002 mmol) pre-dissolved in $CH_3CN$ (200 µL), chlorobenzene (45 µL, 0.45 mmol), and DVB (63.26 µL, 0.45 mmol) were added to the vial. Upon equilibrating to ~0° C. for 20 min using an ice bath, the stirred solution was added aqueous $H_2O_2$ (30 wt %, 74.4 µL, 1.64 equiv, 0.73 mmol) through a micropipette. The vial was subsequently capped and kept at ~0° C. throughout the duration of the reaction.

At each hour, the vial was uncapped and aliquots of the reaction mixture (30 µL) were taken for analysis. Aqueous $H_2O_2$ (30 wt %, 74.4 µL, 1.64 equiv, 0.73 mmol) was added through a micropipette before the vial was closed again. (At the end of the reaction, a total of 595 µL, 13.2 equiv, 5.8 mmol have been added). Each of the aliquots was passed through a glass pipette plug that was prepacked with glass wool, $MgSO_4$ (~5 mg), and Ag powder (~5 mg). The plug was then rinsed with anhydrous $CH_3CN$ (1 mL) and the combined organic was monitored by GC-FID or GC-MS using the aforementioned procedure described in the Methods section. The results of this Example 6 are shown in Table I.

Example 7—Reuse of NU-1000-$A^{L4}$ for Epoxidation of DVB-$3^{rd}$ Cycle

After the 2nd cycle of epoxidation (Example 6), the supernatant solution was decanted from the 2-5 mL microwave vial. To the yellow microcrystalline solid, NU-1000-$A^{L4}$, that remains in the vial was added anhydrous $CH_3CN$ (3 mL). The resultant mixture was left standing for ~12 h. Thereafter, the supernatant solution was decanted from the vial and then new solvent, $CH_3CN$ (3 mL), was added to the vial. This solvent exchange process was repeated three times over a 48 h period.

NU-1000-$A^{L4}$ was collected via filtration over a Buchner funnel, washed with $CH_3CN$, briefly air-dried, and then dried overnight under vacuum at 120° C. NU-1000-$A^{L4}$ (~10.5 mg, 0.004 mmol) was placed into a 2-5 mL microwave vial equipped with a magnetic stir bar. Anhydrous $CH_3CN$ (1 mL), $[Mn_2(TMTACN)_2(\mu-O)_3](PF_6)_2 \cdot H_2O$ (~1.75 mg, 0.002 mmol) pre-dissolved in $CH_3CN$ (200 µL), chlorobenzene (45 µL, 0.45 mmol), and DVB (63.26 µL, 0.45 mmol) were added to the vial. Upon equilibrating to ~0° C. for 20 min using an ice bath, the stirred solution was added aqueous $H_2O_2$ (30 wt %, 74.4 µL, 1.64 equiv, 0.73 mmol) through a micropipette. The vial was subsequently capped and kept at ~0° C. throughout the duration of the reaction.

At each hour, the vial was uncapped and aliquots of the reaction mixture (30 µL) were taken for analysis. Aqueous $H_2O_2$ (30 wt %, 74.4 µL, 1.64 equiv, 0.73 mmol) was added through a micropipette before the vial was closed again. (At the end of the reaction, a total of 670 µL, 14.7 equiv, 6.6 mmol have been added). Each of the aliquots was passed through a glass pipette plug that was prepacked with glass wool, $MgSO_4$ (~5 mg), and Ag powder (~5 mg). The plug was then rinsed with anhydrous $CH_3CN$ (1 mL) and the combined organic was monitored by GC-FID or GC-MS using the aforementioned procedure described in the Methods section. The results of this Example 7 are shown in Table I.

Example 8—Reuse of NU-1000-$A^{L4}$ for Epoxidation of DVB-$4^{rd}$ Cycle

After the 3rd cycle of epoxidation (Example 7), the supernatant solution was decanted from the 2-5 mL microwave vial. To the yellow microcrystalline solid, NU-1000-$A^{L4}$, that remains in the vial was added anhydrous $CH_3CN$ (3 mL). The resultant mixture was left standing for ~12 h. Thereafter, the supernatant solution was decanted from the vial and then new solvent, $CH_3CN$ (3 mL), was added to the vial. This solvent exchange process was repeated three times over a 48 h period.

NU-1000-$A^{L4}$ was collected via filtration over a Buchner funnel, washed with $CH_3CN$, briefly air-dried, and then dried overnight under vacuum at 120° C. NU-1000-$A^{L4}$ (~10.5 mg, 0.004 mmol) was placed into a 2-5 mL microwave vial equipped with a magnetic stir bar. Anhydrous $CH_3CN$ (1 mL), $[Mn_2(TMTACN)_2(\mu-O)_3](PF_6)_2 \cdot H_2O$ (~1.75 mg, 0.002 mmol) pre-dissolved in $CH_3CN$ (200 µL), chlorobenzene (45 µL, 0.45 mmol), and DVB (63.26 µL, 0.45 mmol) were added to the vial. Upon equilibrating to ~0° C. for 20 min using an ice bath, the stirred solution was added aqueous $H_2O_2$ (30 wt %, 74.4 µL, 1.64 equiv, 0.73 mmol) through a micropipette. The vial was subsequently capped and kept at ~0° C. throughout the duration of the reaction.

At each hour, the vial was uncapped and aliquots of the reaction mixture (30 µL) were taken for analysis. Aqueous $H_2O_2$ (30 wt %, 74.4 µL, 1.64 equiv, 0.73 mmol) was added through a micropipette before the vial was closed again. (At the end of the reaction, a total of 774 µL, 16.4 equiv, 7.3 mmol have been added). Each of the aliquots was passed through a glass pipette plug that was prepacked with glass wool, $MgSO_4$ (~5 mg), and Ag powder (~5 mg). The plug was then rinsed with anhydrous $CH_3CN$ (1 mL) and the combined organic was monitored by GC-FID or GC-MS using the aforementioned procedure described in the Methods section. The results of this Example 8 are shown in Table I.

Example 9—Reuse of NU-1000-$A^{L4}$ for Epoxidation of DVB-$5^{th}$ Cycle

After the 4th cycle of epoxidation (Example 8), the supernatant solution was decanted from the 2-5 mL microwave vial. To the yellow microcrystalline solid, NU-1000-$A^{L4}$, that remains in the vial was added anhydrous $CH_3CN$ (3 mL). The resultant mixture was left standing for ~12 h. Thereafter, the supernatant solution was decanted from the vial and then new solvent, $CH_3CN$ (3 mL), was added to the vial. This solvent exchange process was repeated three times over a 48 h period.

NU-1000-$A^{L4}$ was collected via filtration over a Buchner funnel, washed with $CH_3CN$, briefly air-dried, and then dried overnight under vacuum at 120° C. NU-1000-$A^{L4}$ (~10.5 mg, 0.004 mmol) was placed into a 2-5 mL microwave vial equipped with a magnetic stir bar. A solution of 2,3-dichloromaleic anhydride (~3.6 mg, 0.022 mmol, 5 equiv) pre-dissolved in $CH_3CN$ (2 mL) was added to the vial. The vial was capped and then subsequently heated at 80° C. for 24 h without stirring. The resulting reaction mixture was allowed to cool to room temperature and the solvent was decanted. To the resultant yellow microcrystalline solid was added anhydrous $CH_3CN$ (3 mL); and the resulting mixture was left standing for ~12 h before being decanted and replaced with new solvent. This solvent exchange process was repeated three times over a 48 h period.

Reactivated NU-1000-$A^{L4}$ was collected via filtration over a Buchner funnel, washed with $CH_3CN$, briefly air-dried, and then dried overnight under vacuum at 120° C. NU-1000-$A^{L4}$ (~10.5 mg, 0.004 mmol) was placed into a 2-5 mL microwave vial equipped with a magnetic stir bar. Anhydrous $CH_3CN$ (1 mL), $[Mn_2(TMTACN)_2(\mu-O)_3](PF_6)_2 \cdot H_2O$ (~1.75 mg, 0.002 mmol) pre-dissolved in $CH_3CN$ (200 µL), chlorobenzene (45 µL, 0.45 mmol), and DVB (63.26 µL, 0.45 mmol) were added to the vial. Upon equilibrating to ~0° C. for 20 min using an ice bath, the stirred solution was added aqueous $H_2O_2$ (30 wt %, 74.4 µL, 1.64 equiv, 0.73 mmol) through a micropipette. The vial was subsequently capped and kept at ~0° C. throughout the duration of the reaction.

At each hour, the vial was uncapped and aliquots of the reaction mixture (30 µL) were taken for analysis. Aqueous $H_2O_2$ (30 wt %, 74.4 µL, 1.64 equiv, 0.73 mmol) was added through a micropipette before the vial was closed again. (At the end of the reaction, a total of 520 µL, 11.5 equiv, 5.1 mmol have been added). Each of the aliquots was passed through a glass pipette plug that was prepacked with glass wool, $MgSO_4$ (~5 mg), and Ag powder (~5 mg). The plug was then rinsed with anhydrous $CH_3CN$ (1 mL) and the combined organic was monitored by GC-FID or GC-MS using the aforementioned procedure described in the Methods section. The results of this Example 9 are shown in Table I.

Example 10—Filtration of NU-1000-$A^{L3}$ after Epoxidation of DVB-$2^{nd}$ Cycle After the epoxidation in Example 2, the supernatant solution was decanted from the 2-5 mL microwave vial. To the yellow microcrystalline solid, NU-1000-$A^{L3}$, that remains in the vial was added anhydrous $CH_3CN$ (3 mL). The resultant mixture was left standing for ~12 h. Thereafter, the supernatant solution was decanted from the vial and then new solvent, $CH_3CN$ (3 mL), was added to the vial. This solvent exchange process was repeated three times over a 48 h period.

NU-1000-$A^{L3}$ was collected via filtration over a Büchner funnel, washed with $CH_3CN$, briefly air-dried, and then dried overnight under vacuum at 120° C. NU-1000-$A^{L3}$ (~10.1 mg, 0.004 mmol) was placed into a 2-5 mL microwave vial equipped with a magnetic stir bar. Anhydrous $CH_3CN$ (1 mL), $[Mn_2(TMTACN)_2(\mu-O)_3](PF_6)_2 \cdot H_2O$ (~1.75 mg, 0.002 mmol) pre-dissolved in $CH_3CN$ (200 µL), chlorobenzene (45 µL, 0.45 mmol), and DVB (63.26 µL, 0.45 mmol) were added to the vial. Upon equilibrating to ~0° C. for 20 min using an ice bath, the stirred solution was added aqueous $H_2O_2$ (30 wt %, 37.2 µL, 0.82 equiv 0.37 mmol) through a micropipette. The vial was subsequently capped and kept at ~0° C. throughout the duration of the reaction.

After 1 hour, the NU-1000-$A^{L3}$ MOF particles were removed away from the reaction solution by filtration through a glass pipette plug that was prepacked with glass wool. The solution was placed into another 2-5 mL microwave vial equipped with a magnetic stir bar that was chilled to ~0° C. using an ice bath. To the stirred solution was added aqueous $H_2O_2$ (30 wt %, 37.2 µL, 0.82 equiv 0.37 mmol) through a micropipette. The vial was subsequently capped and kept at ~0° C. throughout the duration of the reaction.

At each hour, the vial was uncapped and aliquots of the reaction mixture (30 µL) were taken for analysis. Aqueous $H_2O_2$ (30 wt %, 37.2 µL, 0.82 equiv 0.37 mmol) was added through a micropipette before the vial was closed again. (At the end of the analysis, a total of 223 µL, 4.9 equiv, 2.2 mmol have been added). Each of the aliquots was passed through a glass pipette plug that was prepacked with glass wool, $MgSO_4$ (~5 mg), and Ag powder (~5 mg). The plug was then rinsed with anhydrous $CH_3CN$ (1 mL) and the combined organic was monitored by GC-FID or GC-MS using the aforementioned procedure described in the Methods section. The results of this Example 10 are shown in Table I.

TABLE I

| Example | Catalyst | Temp. (° C.) | Time (hours) | $H_2O_2$ equiv. | DVBDO (% yield) | Selectivity (%) |
|---|---|---|---|---|---|---|
| Comp. Ex. A | NU-1000 | 0 | 24 | 8.2 | 0 | 0 |
| Comp. Ex. B | Butyric acid | 0 | 24 | 8.2 | 35 | 100 |
| Comp. Ex. C | Crotonic acid | 0 | 24 | 8.2 | 70 | 100 |
| Ex. 1 | NU-1000-$A^{L2}$ | 0 | 24 | 8.2 | 84 | 100 |
| Ex. 2 | NU-1000-$A^{L3}$ | 0 | 8 | 8.2 | 93 | 100 |
| Ex. 3 | NU-1000-$A^{L4}$ | 0 | 7 | 5.7 | 100 | 100 |
| Ex. 4 | NU-1000-$A^{L4}$ | 0 | 5 | 8.2 | 100 | 100 |
| Ex. 5 | NU-1000-$A^{L4}$ | 25 | 4.5 | 8.2 | 100 | 100 |
| Ex. 6 | NU-1000-$A^{L4}$-$2^{nd}$ cycle | 0 | 8 | 13.2 | 100 | 100 |
| Ex. 7 | NU-1000-$A^{L4}$-$3^{rd}$ cycle | 0 | 9 | 14.7 | 82 | 100 |
| Ex. 8 | NU-1000-$A^{L4}$-$4^{th}$ cycle | 0 | 10 | 16.4 | 71 | 100 |
| Ex. 9 | NU-1000-$A^{L4}$-$5^{th}$ cycle | 0 | 7 | 11.5 | 100 | 100 |
| Ex. 10 | NU-1000-$A^{L3}$-$2^{nd}$ cycle-filtration | 0 | 6 | 4.9 | 0 | 0 |

We claim:

1. A process for preparing an olefin oxide compound product comprising reacting:
    (A) an olefin compound;
    (B) an oxidant, and
    (C) a catalyst composition comprising (a) a manganese 1,4,7-triazacyclononane (TACN) complex; and (b) a reaction product of a polycrystalline metal organic framework (MOF) comprising a $Zr_6$ metal center coupled to an arene organic component comprising 2-4 carboxylic acid moieties, said MOF comprising a Zr—OH moiety; and a carboxylate compound selected from carboxylic acids, dicarboxylic acids and carboxylic acid anhydrides and combinations thereof, said reaction product comprising a Zr—OH moiety coupled to a carboxylic acid moiety, said manganese complex tethered to said reaction product by a said carboxylic acid moiety, under conditions to prepare an olefin oxide compound product.

2. The process of claim 1, wherein the olefin compound comprises an olefin compound containing multi-olefin functionalities.

3. The process of claim 2, wherein the olefin compound containing multi-olefin functionalities is an aromatic olefin compound; and the multi-olefin oxide compound product prepared from the aromatic olefin compound is an aromatic multi-olefin oxide compound.

4. The process of claim 3, wherein the aromatic olefin compound containing multi-olefin functionalities is a divinylarene compound and the aromatic multi-olefin oxide compound product prepared is a divinylarene dioxide compound.

5. The process of claim 4, wherein the divinylarene compound is divinylbenzene and the divinylarene dioxide compound product prepared is a divinylbenzene dioxide compound.

6. The process of claim 1, wherein the oxidant is a peroxide compound.

7. The process of claim 6, wherein the oxidant is hydrogen peroxide.

8. The process of claim 1, wherein component (a) of the catalyst composition is a 1,4,7-trimethyl-1,4,7-triazacyclononane (TMTACN) manganese complex and wherein the MOF of component (b) of the catalyst composition is $Zr_6(OH)_8(TBAPy)_2$, wherein TBAPy is 1,3,6,8-tetrakis(p-benzoic acid) pyrene.

9. The process of claim 1, wherein the process reaction is carried out at a temperature of from about 0° C. to about 40° C.

10. The process of claim 9, wherein the process reaction is carried out at a temperature of from about 0° C. to about 25° C.

11. The process of claim 1, including further (d) a solvent in the reaction mixture.

12. The process of claim 11, wherein the solvent comprises acetonitrile.

13. The process of claim 1, including further the step of recovering the catalyst composition from the reaction mixture.

14. The process of claim 13, including further the step of regenerating the catalyst composition.

15. The process of claim 1, wherein the concentration of the olefin compound ranges from about 0.01 M to about 10 M; wherein the concentration of the oxidant is such that the molar ratio of oxidant per double bond of the olefin compound is from about 3:1 to about 8:1; and wherein the concentration of the catalyst composition per double bond of the olefin compound ranges from about 0.05 mol % to about 5 mol %.

* * * * *